(12) United States Patent
Smirnov et al.

(10) Patent No.: US 7,670,822 B2
(45) Date of Patent: Mar. 2, 2010

(54) ALDOLASE AND PRODUCTION PROCESS OF 4-HYDROXY-L-ISOLEUCINE

(75) Inventors: Sergey Vasilievich Smirnov, Moscow (RU); Natalia Nikolaevna Samsonova, Moscow (RU); Tomohiro Kodera, Kawasaki (JP); Kazuhiko Matsui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/212,767

(22) Filed: Sep. 18, 2008

(65) Prior Publication Data

US 2009/0104659 A1 Apr. 23, 2009

Related U.S. Application Data

(63) Continuation of application No. PCT/JP2007/056756, filed on Mar. 22, 2007.

(30) Foreign Application Priority Data

Mar. 24, 2006 (RU) ............................... 2006109216

(51) Int. Cl.
*C07H 21/04* (2006.01)
*C12N 9/88* (2006.01)
(52) U.S. Cl. ............... 435/232; 435/252.3; 435/252.33; 435/320.1; 536/23.2; 536/23.1
(58) Field of Classification Search ........................ None
See application file for complete search history.

(56) References Cited

U.S. PATENT DOCUMENTS

| 7,090,998 | B2 | 8/2006 | Ishikawa et al. |
| 7,252,972 | B2 | 8/2007 | Kikuchi et al. |
| 7,306,933 | B2 | 12/2007 | Dien et al. |
| 7,468,262 | B2 | 12/2008 | Usuda et al. |
| 2004/0229305 | A1 | 11/2004 | Usuda et al. |
| 2004/0265956 | A1 | 12/2004 | Takikawa et al. |
| 2005/0181488 | A1 | 8/2005 | Akhverdian et al. |
| 2006/0234356 | A1 | 10/2006 | Usuda et al. |
| 2006/0234357 | A1 | 10/2006 | Usuda et al. |

FOREIGN PATENT DOCUMENTS

| WO | WO97/32577 | 9/1997 |
| WO | WO2006/093322 | 9/2006 |

OTHER PUBLICATIONS

Broca, C., et al., "4-Hydroxyisoleucine: effects of synthetic and natural analogues on insulin secretion," Eur. J. Pharmcol. 2000;390:339-345.
Smirnov, S. V., et al., "A novel strategy for enzymatic synthesis of 4-hydroxyisoleucine: identification of an enzyme possessing HMKP (-hydroxy-3-methyl-2-keto-pentanoate) aldolase activity," FEMS Microbiol. Lett. 2007;273:70-77.
International Search Report for PCT Patent App. No. PCT/JP2007/056756 (Jul. 31, 2007).
Haefelé, C., et al., "Characterization of a Dioxygenase from *Trigonella Foenum-Graecyn* Involved in 4-Hydroxyisoleucine Biosynthesis," Phytochemistry 1997;44(4):563-566.
Ogawa, J., et al., "Synthesis of 4-Hydroxyisoleucine by the Aldolase-Transaminase Coupling Reaction and Basic Characterization of the Aldolase from *Arthrobacter simplex* AKU 626," Biosei. Biotechnol. Biochem. 2007;71(7):1607-1615.
International Preliminary Report on Patentability for PCT Patent App. No. PCT/JP2007/056756 (Oct. 9, 2008).
U.S. Appl. No. 11/877726, Van Dien et al., filed Oct. 24, 2007.
U.S. Appl. No. 12/055438, Iwatani et al., filed Mar. 26, 2008.
U.S. Appl. No. 61/058313, Ermishev et al., Filed Jun. 3, 2008.
U.S. Appl. No. 12/202476, Terashita et al., Filed Sep. 2, 2008.

*Primary Examiner*—Nashaat T Nashed
(74) *Attorney, Agent, or Firm*—Shelly Guest Cermak; Cermak Kenealy Vaidya & Nakajima LLP

(57) ABSTRACT

A novel aldolase is described. 4-hydroxy-3-methyl-2-keto-pentanoic acid, which is useful as an intermediate in the synthesis of 4-hydroxy-L-isoleucine, may be synthesized from acetaldehyde and α-ketobutyric acid using a novel aldolase, which is derived from the genus *Arthrobacter*.

4 Claims, 7 Drawing Sheets

A) SEQ ID NO.:3  NH₂-P F P V E L P D N F A K R V T D S D S A Q V G L F I...-COOH

B) SEQ ID NO:4  5'-cggcctcctgtttagctcccg-atg-ccI-tt(t/c)-ccI-gtI-ga(a/g)-(c/t)tI-ccI-ga(t/c)-aa(t/c)-tt(t/c)-3'

C) SEQ ID NO: 5  5'-cggcctcctgtttagctcccg-3'

FIG. 4

```
              1                                                                   70
HHDE_BLI   (1) MPFQVELPQTFTQRVAKLGAGEHLAGMWVCSGSPVAAEIAAASGMQWVLIDAEHSPIDLQITTSLLQAMN
 asiHPAL   (1) MPFPVELPDNFAKRVTDSDS--AQVGLFISSGSETNAEIVASAGFDWLLIDAEHSPYGLETVTSLLRTVA
              71                                                                  140
HHDE_BLI  (71) GYPATPVVRVPVNDQVLIKQYLDLGAQNLLVPMVDTPADAEAAVRSVYYPPRGVRGVGSALARASRWNAV
 asiHPAL  (69) AYPATPVVRTPVNDTVLIKQYLDLGAQNLMVPMVHNAEQAEKAVAAMHYPPRGVRGIGAALARSSRFNGV
              141                                                                 210
HHDE_BLI (141) PNYLARAEDFVSLTIQIESATAVDNAAEIAAVDGVDAVFVGPSDLAASMGLLGQQTHPDVTDAVLRTFDA
 asiHPAL (139) DDYLNKASETVSLTVQVESAEAVENAAEVAAVDGVDALFIGPSDLAASMGLLGQQQHPAVLAAVDTTFKA
              211                                    262
HHDE_BLI (211) VKAAGKLVGVNAFDPDQARKYLDAGASFVLVGADVGLMMNGARAWAKTWVQD stop SEQ ID NO: 18
 asiHPAL (180) VRDAGKLVGINAFNLAQAQAYIXAGASFVCVGADVQQLASATRALVEKFKG- stop SEQ ID NO: 2
```

FIG. 7

SEQUENCE LISTING

```
<160> NUMBER OF SEQ ID NOS: 18

<210> SEQ ID NO 1
<211> LENGTH: 780
<212> TYPE: DNA
<213> ORGANISM: Arthrobacter simplex
<220> FEATURE:
<221> NAME/KEY: CDS
<222> LOCATION: (1)..(780)

<400> SEQUENCE: 1 atg ccg ttt ccg gtg gag ttg ccg gat aat ttc gcc aag cgc gtc acc        48
Met Pro Phe Pro Val Glu Leu Pro Asp Asn Phe Ala Lys Arg Val Thr
1               5                   10                  15 gat tcg gac agt gcg cag gta gga ctc ttc atc tcg tcg ggc tcg gaa        96
Asp Ser Asp Ser Ala Gln Val Gly Leu Phe Ile Ser Ser Gly Ser Glu
                20                  25                  30 acc aat gca gag atc gtc gct tcc gca ggc ttc gat tgg ctg ctt atc       144
Thr Asn Ala Glu Ile Val Ala Ser Ala Gly Phe Asp Trp Leu Leu Ile
            35                  40                  45 gat gcc gag cac tcc cct tac ggc ctt gaa acc gtc acc agc ttg ttg       192
Asp Ala Glu His Ser Pro Tyr Gly Leu Glu Thr Val Thr Ser Leu Leu
        50                  55                  60 cgc act gtt gcg gcc tat cct gct acc cca gtg gta cgg att cca gtc       240
Arg Thr Val Ala Ala Tyr Pro Ala Thr Pro Val Val Arg Ile Pro Val
65                  70                  75                  80 aac gac aca gtg ctg atc aag cag tac ctg gac ttg ggt gcg caa aac       288
Asn Asp Thr Val Leu Ile Lys Gln Tyr Leu Asp Leu Gly Ala Gln Asn
                85                  90                  95 ctc atg gtt ccg atg gtg cac aac gcc gag caa gcc gaa aag gca gtc       336
Leu Met Val Pro Met Val His Asn Ala Glu Gln Ala Glu Lys Ala Val
                100                 105                 110 gcc gcg atg cac tat cca ccc cgc gga gtt cgc ggt atc ggt gca gca       384
Ala Ala Met His Tyr Pro Pro Arg Gly Val Arg Gly Ile Gly Ala Ala
            115                 120                 125 ctg gca cgt tcc tcc cgg ttc aat ggc gtc gat gac tac ctg aac aag       432
Leu Ala Arg Ser Ser Arg Phe Asn Gly Val Asp Asp Tyr Leu Asn Lys
        130                 135                 140 gcg agc gag acc gtg agc ctt acc gtc cag gtc gag tct gcc gaa gcg       480
Ala Ser Glu Thr Val Ser Leu Thr Val Gln Val Glu Ser Ala Glu Ala
145                 150                 155                 160 gta gaa aac gcc gca gaa gtc gct gcc gtc gat ggc gtc gat gct atc       528
Val Glu Asn Ala Ala Glu Val Ala Ala Val Asp Gly Val Asp Ala Ile
                165                 170                 175 ttc atc ggc cct tcc gac ttg gct gct tcc atg ggt ctt tta ggc cag       576
Phe Ile Gly Pro Ser Asp Leu Ala Ala Ser Met Gly Leu Leu Gly Gln
                180                 185                 190 caa cag cac cct gcc gtg ctt gct gct gtg gat acg acc ttc aag gca       624
Gln Gln His Pro Ala Val Leu Ala Ala Val Asp Thr Thr Phe Lys Ala
            195                 200                 205
```

```
gtc cgc gat gca ggc aag ctc gtt ggc atc aat gcc ttc aat ctc gca     672
Val Arg Asp Ala Gly Lys Leu Val Gly Ile Asn Ala Phe Asn Leu Ala
    210                 215                 220 caa gcc cag gcc tat atc gat gct ggc gca tct ttt gtc tgc gtc ggc     720
Gln Ala Gln Ala Tyr Ile Asp Ala Gly Ala Ser Phe Val Cys Val Gly
225                 230                 235                 240 gct gat gtt cag cag ttg gcg agt gct acc cgt gcc ctc gtg gag aag     768
Ala Asp Val Gln Gln Leu Ala Ser Ala Thr Arg Ala Leu Val Glu Lys
                245                 250                 255 ttc aag ggc tag                                                     780
Phe Lys Gly <210> SEQ ID NO 2
<211> LENGTH: 259
<212> TYPE: PRT
<213> ORGANISM: Arthrobacter simplex

<400> SEQUENCE: 2

Met Pro Phe Pro Val Glu Leu Pro Asp Asn Phe Ala Lys Arg Val Thr
1               5                   10                  15

Asp Ser Asp Ser Ala Gln Val Gly Leu Phe Ile Ser Ser Gly Ser Glu
            20                  25                  30

Thr Asn Ala Glu Ile Val Ala Ser Ala Gly Phe Asp Trp Leu Leu Ile
        35                  40                  45

Asp Ala Glu His Ser Pro Tyr Gly Leu Glu Thr Val Thr Ser Leu Leu
    50                  55                  60

Arg Thr Val Ala Ala Tyr Pro Ala Thr Pro Val Val Arg Ile Pro Val
65                  70                  75                  80

Asn Asp Thr Val Leu Ile Lys Gln Tyr Leu Asp Leu Gly Ala Gln Asn
                85                  90                  95

Leu Met Val Pro Met Val His Asn Ala Glu Gln Ala Glu Lys Ala Val
            100                 105                 110

Ala Ala Met His Tyr Pro Pro Arg Gly Val Arg Gly Ile Gly Ala Ala
        115                 120                 125

Leu Ala Arg Ser Ser Arg Phe Asn Gly Val Asp Asp Tyr Leu Asn Lys
    130                 135                 140

Ala Ser Glu Thr Val Ser Leu Thr Val Gln Val Glu Ser Ala Glu Ala
145                 150                 155                 160

Val Glu Asn Ala Ala Glu Val Ala Ala Val Asp Gly Val Asp Ala Ile
                165                 170                 175

Phe Ile Gly Pro Ser Asp Leu Ala Ala Ser Met Gly Leu Leu Gly Gln
            180                 185                 190

Gln Gln His Pro Ala Val Leu Ala Ala Val Asp Thr Thr Phe Lys Ala
        195                 200                 205

Val Arg Asp Ala Gly Lys Leu Val Gly Ile Asn Ala Phe Asn Leu Ala
    210                 215                 220

Gln Ala Gln Ala Tyr Ile Asp Ala Gly Ala Ser Phe Val Cys Val Gly
225                 230                 235                 240

Ala Asp Val Gln Gln Leu Ala Ser Ala Thr Arg Ala Leu Val Glu Lys
                245                 250                 255

Phe Lys Gly

<210> SEQ ID NO 3
<211> LENGTH: 26
<212> TYPE: PRT
<213> ORGANISM: Arthrobacter simplex
```

-continued

<400> SEQUENCE: 3

Pro Phe Pro Val Glu Leu Pro Asp Asn Phe Ala Lys Arg Val Thr Asp
1               5                   10                  15

Ser Asp Ser Ala Gln Val Gly Leu Phe Ile
            20                  25

<210> SEQ ID NO 4
<211> LENGTH: 54
<212> TYPE: DNA
<213> ORGANISM: Artificial sequence
<220> FEATURE:
<223> OTHER INFORMATION: primer asiN10
<220> FEATURE:
<221> NAME/KEY: modified_base
<222> LOCATION: (27)..(45)
<223> OTHER INFORMATION: n = inosine
<220> FEATURE:
<221> NAME/KEY: misc_feature
<222> LOCATION: (27)..(54)
<223> OTHER INFORMATION: y = t or c; r = a or g

<400> SEQUENCE: 4
cggcctcctg tttagctccc gatgccntty ccngtngary tnccngayaa ytty           54

<210> SEQ ID NO 5
<211> LENGTH: 21
<212> TYPE: DNA
<213> ORGANISM: Artificial sequence
<220> FEATURE:
<223> OTHER INFORMATION: primer SVS88

<400> SEQUENCE: 5
cggcctcctg tttagctccc g                                              21

<210> SEQ ID NO 6
<211> LENGTH: 24
<212> TYPE: DNA
<213> ORGANISM: Artificial sequence
<220> FEATURE:
<223> OTHER INFORMATION: primer SVS_108

<400> SEQUENCE: 6
acttgggtgc gcaaaacctc atgg                                           24

<210> SEQ ID NO 7
<211> LENGTH: 24
<212> TYPE: DNA
<213> ORGANISM: Artificial sequence
<220> FEATURE:
<223> OTHER INFORMATION: primer SVS_109

<400> SEQUENCE: 7
ccatgaggtt ttgcgcaccc aagt                                           24

<210> SEQ ID NO 8
<211> LENGTH: 37
<212> TYPE: DNA
<213> ORGANISM: Artificial sequence
<220> FEATURE:
<223> OTHER INFORMATION: primer

<400> SEQUENCE: 8
cgtcaagctt acatatgccg tttccggtgg agttgcc                             37

<210> SEQ ID NO 9

<211> LENGTH: 35
<212> TYPE: DNA
<213> ORGANISM: Artificial sequence
<220> FEATURE:
<223> OTHER INFORMATION: primer

<400> SEQUENCE: 9
cgtacctagg ctagcccttg aacttctcca cgagg            35

<210> SEQ ID NO 10
<211> LENGTH: 72
<212> TYPE: DNA
<213> ORGANISM: Artificial sequence
<220> FEATURE:
<223> OTHER INFORMATION: primer

<400> SEQUENCE: 10
ctgaccatgg gcagcagcca tcatcatcat catcacagca gcggcactaa acaaacaatt            60
cgcgttgaat tg            72

<210> SEQ ID NO 11
<211> LENGTH: 35
<212> TYPE: DNA
<213> ORGANISM: Artificial sequence
<220> FEATURE:
<223> OTHER INFORMATION: primer

<400> SEQUENCE: 11
ctgagcggcc gcttacttgc tttcagtcag cgctg            35

<210> SEQ ID NO 12
<211> LENGTH: 20
<212> TYPE: DNA
<213> ORGANISM: Artificial sequence
<220> FEATURE:
<223> OTHER INFORMATION: primer T7

<400> SEQUENCE: 12
taatacgact cactataggg            20

<210> SEQ ID NO 13
<211> LENGTH: 284
<212> TYPE: PRT
<213> ORGANISM: Artificial sequence
<220> FEATURE:
<223> OTHER INFORMATION: COG0115

<400> SEQUENCE: 13

Ala Gly Lys Ile Trp Val Asn Gly Glu Leu Val Pro Glu Glu Asp Ala
1               5                   10                  15

Lys Leu Ser Val Leu Asp Arg Gly Leu His Tyr Gly Asp Gly Val Phe
            20                  25                  30

Glu Thr Leu Arg Ala Tyr Asn Gly Lys Leu Phe Arg Leu Asp Glu His
        35                  40                  45

Leu Ala Arg Leu Lys Arg Ser Ala Lys Arg Leu Gly Leu Pro Arg Pro
    50                  55                  60

Glu Ser Glu Glu Glu Ile Glu Leu Leu Ile Gln Leu Leu Ala Lys
65                  70                  75                  80

Asn Asn Leu Val Pro Gly Leu Tyr Ile Arg Pro Leu Val Arg Gly Gly
                85                  90                  95

Gly Gly Gly Leu Gly Val Arg Asp Ala Thr Glu Pro Thr Leu Ile Val
            100                 105                 110

```
Ala Ala Ser Pro Val Gly Ala Tyr Leu Lys Gly Gly Arg Leu Glu Lys
        115                 120                 125

Gly Val Val Leu Val Ile Ser Ser Pro Val Arg Arg Ala Pro Pro Gly
    130                 135                 140

Pro Gly Ala Ala Lys Lys Thr Gly Asn Tyr Leu Ser Ser Val Leu Ala
145                 150                 155                 160

Lys Arg Glu Ala Lys Ala Ala Gly Ala Asp Glu Ala Leu Leu Leu Asp
                165                 170                 175

Glu Asp Gly Tyr Val Thr Glu Gly Ala Gly Ser Asn Val Phe Phe Val
            180                 185                 190

Lys Gly Asp Gly Val Leu Val Thr Pro Pro Leu Ser Gly Gly Ile Leu
        195                 200                 205

Pro Gly Ile Thr Arg Asp Ser Leu Leu Glu Leu Ala Lys Glu Leu Gly
    210                 215                 220

Leu Thr Val Glu Glu Arg Pro Ile Thr Leu Glu Asp Leu Lys Gln Ala
225                 230                 235                 240

Asp Glu Val Phe Leu Thr Asn Thr Ala Ala Gly Val Thr Pro Val Gly
                245                 250                 255

Leu Ile Asp Gly Arg Val Gly Gln Pro Gly Pro Val Thr Lys Lys Leu
            260                 265                 270

Arg Glu Leu Leu Thr Asp Ile Gln Tyr Gly Glu Ile
        275                 280
```

<210> SEQ ID NO 14
<211> LENGTH: 930
<212> TYPE: DNA
<213> ORGANISM: Escherichia coli
<220> FEATURE:
<221> NAME/KEY: CDS
<222> LOCATION: (1)..(930)
<220> FEATURE:
<221> NAME/KEY: misc_feature
<223> OTHER INFORMATION: ilvE

<400> SEQUENCE: 14

```
atg acc acg aag aaa gct gat tac att tgg ttc aat ggg gag atg gtt    48
Met Thr Thr Lys Lys Ala Asp Tyr Ile Trp Phe Asn Gly Glu Met Val
1               5                   10                  15 cgc tgg gaa gac gcg aag gtg cat gtg atg tcg cac gcg ctg cac tat    96
Arg Trp Glu Asp Ala Lys Val His Val Met Ser His Ala Leu His Tyr
                20                  25                  30 ggc act tcg gtt ttt gaa ggc atc cgt tgc tac gac tcg cac aaa gga   144
Gly Thr Ser Val Phe Glu Gly Ile Arg Cys Tyr Asp Ser His Lys Gly
            35                  40                  45 ccg gtt gta ttc cgc cat cgt gag cat atg cag cgt ctg cat gac tcc   192
Pro Val Val Phe Arg His Arg Glu His Met Gln Arg Leu His Asp Ser
        50                  55                  60 gcc aaa atc tat cgc ttc ccg gtt tcg cag agc att gat gag ctg atg   240
Ala Lys Ile Tyr Arg Phe Pro Val Ser Gln Ser Ile Asp Glu Leu Met
65                  70                  75                  80 gaa gct tgt cgt gac gtg atc cgc aaa aac aat ctc acc agc gcc tat   288
Glu Ala Cys Arg Asp Val Ile Arg Lys Asn Asn Leu Thr Ser Ala Tyr
                85                  90                  95 atc cgt ccg ctg atc ttc gtc ggt gat gtt ggc atg gga gta aac ccg   336
Ile Arg Pro Leu Ile Phe Val Gly Asp Val Gly Met Gly Val Asn Pro
            100                 105                 110 cca gcg gga tac tca acc gac gtg att atc gct gct ttc ccg tgg gga   384
Pro Ala Gly Tyr Ser Thr Asp Val Ile Ile Ala Ala Phe Pro Trp Gly
        115                 120                 125
```

```
gcg tat ctg ggc gca gaa gcg ctg gag cag ggg atc gat gcg atg gtt      432
Ala Tyr Leu Gly Ala Glu Ala Leu Glu Gln Gly Ile Asp Ala Met Val
    130                 135                 140 tcc tcc tgg aac cgc gca gca cca aac acc atc ccg acg gcg gca aaa      480
Ser Ser Trp Asn Arg Ala Ala Pro Asn Thr Ile Pro Thr Ala Ala Lys
145                 150                 155                 160 gcc ggt ggt aac tac ctc tct tcc ctg ctg gtg ggt agc gaa gcg cgc      528
Ala Gly Gly Asn Tyr Leu Ser Ser Leu Leu Val Gly Ser Glu Ala Arg
                165                 170                 175 cgc cac ggt tat cag gaa ggt atc gcg ctg gat gtg aac ggt tat atc      576
Arg His Gly Tyr Gln Glu Gly Ile Ala Leu Asp Val Asn Gly Tyr Ile
            180                 185                 190 tct gaa ggc gca ggc gaa aac ctg ttt gaa gtg aaa gat ggt gtg ctg      624
Ser Glu Gly Ala Gly Glu Asn Leu Phe Glu Val Lys Asp Gly Val Leu
        195                 200                 205 ttc acc cca ccg ttc acc tcc tcc gcg ctg ccg ggt att acc cgt gat      672
Phe Thr Pro Pro Phe Thr Ser Ser Ala Leu Pro Gly Ile Thr Arg Asp
    210                 215                 220 gcc atc atc aaa ctg gcg aaa gag ctg gga att gaa gta cgt gag cag      720
Ala Ile Ile Lys Leu Ala Lys Glu Leu Gly Ile Glu Val Arg Glu Gln
225                 230                 235                 240 gtg ctg tcg cgc gaa tcc ctg tac ctg gcg gat gaa gtg ttt atg tcc      768
Val Leu Ser Arg Glu Ser Leu Tyr Leu Ala Asp Glu Val Phe Met Ser
                245                 250                 255 ggt acg gcg gca gaa atc acg cca gtg cgc agc gta gac ggt att cag      816
Gly Thr Ala Ala Glu Ile Thr Pro Val Arg Ser Val Asp Gly Ile Gln
            260                 265                 270 gtt ggc gaa ggc cgt tgt ggc ccg gtt acc aaa cgc att cag caa gcc      864
Val Gly Glu Gly Arg Cys Gly Pro Val Thr Lys Arg Ile Gln Gln Ala
        275                 280                 285 ttc ttc ggc ctc ttc act ggc gaa acc gaa gat aaa tgg ggc tgg tta      912
Phe Phe Gly Leu Phe Thr Gly Glu Thr Glu Asp Lys Trp Gly Trp Leu
    290                 295                 300 gat caa gtt aat caa taa                                              930
Asp Gln Val Asn Gln
305

<210> SEQ ID NO 15
<211> LENGTH: 309
<212> TYPE: PRT
<213> ORGANISM: Escherichia coli

<400> SEQUENCE: 15

Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
            20                  25                  30

Gly Thr Ser Val Phe Glu Gly Ile Arg Cys Tyr Asp Ser His Lys Gly
        35                  40                  45

Pro Val Val Phe Arg His Arg Glu His Met Gln Arg Leu His Asp Ser
    50                  55                  60

Ala Lys Ile Tyr Arg Phe Pro Val Ser Gln Ser Ile Asp Glu Leu Met
65                  70                  75                  80

Glu Ala Cys Arg Asp Val Ile Arg Lys Asn Asn Leu Thr Ser Ala Tyr
                85                  90                  95

Ile Arg Pro Leu Ile Phe Val Gly Asp Val Gly Met Gly Val Asn Pro
            100                 105                 110

Pro Ala Gly Tyr Ser Thr Asp Val Ile Ile Ala Ala Phe Pro Trp Gly
        115                 120                 125
```

```
Ala Tyr Leu Gly Ala Glu Ala Leu Glu Gln Gly Ile Asp Ala Met Val
    130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
            180                 185                 190

Ser Glu Gly Ala Gly Glu Asn Leu Phe Glu Val Lys Asp Gly Val Leu
        195                 200                 205

Phe Thr Pro Pro Phe Thr Ser Ser Ala Leu Pro Gly Ile Thr Arg Asp
    210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
            260                 265                 270

Val Gly Glu Gly Arg Cys Gly Pro Val Thr Lys Arg Ile Gln Gln Ala
        275                 280                 285

Phe Phe Gly Leu Phe Thr Gly Glu Thr Glu Asp Lys Trp Gly Trp Leu
    290                 295                 300

Asp Gln Val Asn Gln
305

<210> SEQ ID NO 16
<211> LENGTH: 1092
<212> TYPE: DNA
<213> ORGANISM: Bacillus subtilis
<220> FEATURE:
<221> NAME/KEY: CDS
<222> LOCATION: (1)..(1092)
<220> FEATURE:
<221> NAME/KEY: misc_feature
<223> OTHER INFORMATION: ywaA

<400> SEQUENCE: 16 atg act aaa caa aca att cgc gtt gaa ttg aca tca aca aaa aaa ccg      48
Met Thr Lys Gln Thr Ile Arg Val Glu Leu Thr Ser Thr Lys Lys Pro
1               5                   10                  15 aaa cca gac cca aat cag ctt tcg ttc gga aga gtg ttt aca gac cac      96
Lys Pro Asp Pro Asn Gln Leu Ser Phe Gly Arg Val Phe Thr Asp His
            20                  25                  30 atg ttt gta atg gac tat gcc gca gat aaa ggt tgg tac gat cca aga     144
Met Phe Val Met Asp Tyr Ala Ala Asp Lys Gly Trp Tyr Asp Pro Arg
        35                  40                  45 atc att cct tat caa ccc tta tca atg gat cca act gca atg gtc tat     192
Ile Ile Pro Tyr Gln Pro Leu Ser Met Asp Pro Thr Ala Met Val Tyr
    50                  55                  60 cac tac ggc caa acc gtg ttt gaa ggg tta aag gct tac gtg tca gag     240
His Tyr Gly Gln Thr Val Phe Glu Gly Leu Lys Ala Tyr Val Ser Glu
65                  70                  75                  80 gat gac cat gtt ctg ctt ttc aga ccg gaa aaa aat atg gaa cgc ctg     288
Asp Asp His Val Leu Leu Phe Arg Pro Glu Lys Asn Met Glu Arg Leu
                85                  90                  95 aat caa tca aac gac cgc ctc tgc atc ccg caa att gat gaa gaa cag     336
Asn Gln Ser Asn Asp Arg Leu Cys Ile Pro Gln Ile Asp Glu Glu Gln
            100                 105                 110
```

```
gtt ctt gaa ggc tta aag cag ctt gtc gca att gat aaa gac tgg att      384
Val Leu Glu Gly Leu Lys Gln Leu Val Ala Ile Asp Lys Asp Trp Ile
    115                 120                 125 cca aat gcg gag ggc acg tcc ctt tac atc cgt ccg ttc atc atc gca      432
Pro Asn Ala Glu Gly Thr Ser Leu Tyr Ile Arg Pro Phe Ile Ile Ala
130                 135                 140 acc gag cct ttc ctt ggt gtt gcg gca tct cat acg tat aag ctc ttg      480
Thr Glu Pro Phe Leu Gly Val Ala Ala Ser His Thr Tyr Lys Leu Leu
145                 150                 155                 160 atc att ctt tct ccg gtc ggc tct tat tac aaa gaa ggc att aag ccg      528
Ile Ile Leu Ser Pro Val Gly Ser Tyr Tyr Lys Glu Gly Ile Lys Pro
            165                 170                 175 gtc aaa atc gct gtt gaa agt gaa ttt gtc cgt gcg gta aaa ggc gga      576
Val Lys Ile Ala Val Glu Ser Glu Phe Val Arg Ala Val Lys Gly Gly
        180                 185                 190 aca gga aat gcc aaa acc gca gga aac tat gct tca agc tta aaa gcg      624
Thr Gly Asn Ala Lys Thr Ala Gly Asn Tyr Ala Ser Ser Leu Lys Ala
    195                 200                 205 cag cag gta gcc gaa gag aaa gga ttt tct caa gta ctc tgg ctg gac      672
Gln Gln Val Ala Glu Glu Lys Gly Phe Ser Gln Val Leu Trp Leu Asp
210                 215                 220 ggc att gag aag aaa tac atc gaa gaa gtc gga agc atg aac atc ttc      720
Gly Ile Glu Lys Lys Tyr Ile Glu Glu Val Gly Ser Met Asn Ile Phe
225                 230                 235                 240 ttc aaa atc aac ggt gaa atc gta aca ccg atg ctg aac ggg agc atc      768
Phe Lys Ile Asn Gly Glu Ile Val Thr Pro Met Leu Asn Gly Ser Ile
            245                 250                 255 ctg gaa ggc att acg cgc aat tca gtc atc gcc ttg ctt aag cat tgg      816
Leu Glu Gly Ile Thr Arg Asn Ser Val Ile Ala Leu Leu Lys His Trp
        260                 265                 270 ggc ctt caa gtt tca gaa cga aaa att gcg atc gat gag gtc atc caa      864
Gly Leu Gln Val Ser Glu Arg Lys Ile Ala Ile Asp Glu Val Ile Gln
    275                 280                 285 gcc cat aaa gac ggc atc ctg gaa gaa gcc ttc gga aca ggt aca gca      912
Ala His Lys Asp Gly Ile Leu Glu Glu Ala Phe Gly Thr Gly Thr Ala
290                 295                 300 gct gtt att tcc cca gtc ggc gag ctg atc tgg cag gat gaa aca ctt      960
Ala Val Ile Ser Pro Val Gly Glu Leu Ile Trp Gln Asp Glu Thr Leu
305                 310                 315                 320 tcg atc aac aac ggt gaa aca gga gaa atc gca aaa aaa cta tat gac     1008
Ser Ile Asn Asn Gly Glu Thr Gly Glu Ile Ala Lys Lys Leu Tyr Asp
            325                 330                 335 acg att aca ggc att caa aaa ggc gct gtc gca gac gaa ttc gga tgg     1056
Thr Ile Thr Gly Ile Gln Lys Gly Ala Val Ala Asp Glu Phe Gly Trp
        340                 345                 350 acg acc gaa gtc gca gcg ctg act gaa agc aag taa                     1092
Thr Thr Glu Val Ala Ala Leu Thr Glu Ser Lys
355                 360
```

<210> SEQ ID NO 17
<211> LENGTH: 363
<212> TYPE: PRT
<213> ORGANISM: Bacillus subtilis

<400> SEQUENCE: 17

Met Thr Lys Gln Thr Ile Arg Val Glu Leu Thr Ser Thr Lys Lys Pro
1               5                   10                  15

Lys Pro Asp Pro Asn Gln Leu Ser Phe Gly Arg Val Phe Thr Asp His
            20                  25                  30

Met Phe Val Met Asp Tyr Ala Ala Asp Lys Gly Trp Tyr Asp Pro Arg

```
                35                  40                  45
Ile Ile Pro Tyr Gln Pro Leu Ser Met Asp Pro Thr Ala Met Val Tyr
    50                  55                  60

His Tyr Gly Gln Thr Val Phe Glu Gly Leu Lys Ala Tyr Val Ser Glu
 65                  70                  75                  80

Asp Asp His Val Leu Leu Phe Arg Pro Glu Lys Asn Met Glu Arg Leu
                 85                  90                  95

Asn Gln Ser Asn Asp Arg Leu Cys Ile Pro Gln Ile Asp Glu Glu Gln
            100                 105                 110

Val Leu Glu Gly Leu Lys Gln Leu Val Ala Ile Asp Lys Asp Trp Ile
        115                 120                 125

Pro Asn Ala Glu Gly Thr Ser Leu Tyr Ile Arg Pro Phe Ile Ile Ala
    130                 135                 140

Thr Glu Pro Phe Leu Gly Val Ala Ala Ser His Thr Tyr Lys Leu Leu
145                 150                 155                 160

Ile Ile Leu Ser Pro Val Gly Ser Tyr Tyr Lys Glu Gly Ile Lys Pro
                165                 170                 175

Val Lys Ile Ala Val Glu Ser Glu Phe Val Arg Ala Val Lys Gly Gly
            180                 185                 190

Thr Gly Asn Ala Lys Thr Ala Gly Asn Tyr Ala Ser Ser Leu Lys Ala
        195                 200                 205

Gln Gln Val Ala Glu Glu Lys Gly Phe Ser Gln Val Leu Trp Leu Asp
    210                 215                 220

Gly Ile Glu Lys Lys Tyr Ile Glu Glu Val Gly Ser Met Asn Ile Phe
225                 230                 235                 240

Phe Lys Ile Asn Gly Glu Ile Val Thr Pro Met Leu Asn Gly Ser Ile
                245                 250                 255

Leu Glu Gly Ile Thr Arg Asn Ser Val Ile Ala Leu Leu Lys His Trp
            260                 265                 270

Gly Leu Gln Val Ser Glu Arg Lys Ile Ala Ile Asp Glu Val Ile Gln
        275                 280                 285

Ala His Lys Asp Gly Ile Leu Glu Glu Ala Phe Gly Thr Gly Thr Ala
    290                 295                 300

Ala Val Ile Ser Pro Val Gly Glu Leu Ile Trp Gln Asp Glu Thr Leu
305                 310                 315                 320

Ser Ile Asn Asn Gly Glu Thr Gly Glu Ile Ala Lys Lys Leu Tyr Asp
                325                 330                 335

Thr Ile Thr Gly Ile Gln Lys Gly Ala Val Ala Asp Glu Phe Gly Trp
            340                 345                 350

Thr Thr Glu Val Ala Ala Leu Thr Glu Ser Lys
        355                 360

<210> SEQ ID NO 18
<211> LENGTH: 262
<212> TYPE: PRT
<213> ORGANISM: Brevibacterium linens

<400> SEQUENCE: 18

Met Pro Phe Gln Val Glu Leu Pro Gln Thr Phe Thr Gln Arg Val Ala
  1               5                  10                  15

Lys Leu Gly Ala Gly Glu His Leu Ala Gly Met Trp Val Cys Ser Gly
             20                  25                  30

Ser Pro Val Ala Ala Glu Ile Ala Ala Ala Ser Gly Met Gln Trp Val
         35                  40                  45
```

-continued

```
Leu Ile Asp Ala Glu His Ser Pro Ile Asp Leu Gln Ile Thr Thr Ser
 50                  55                  60
Leu Leu Gln Ala Met Asn Gly Tyr Pro Ala Thr Pro Val Val Arg Val
 65              70                  75                  80
Pro Val Asn Asp Gln Val Leu Ile Lys Gln Tyr Leu Asp Leu Gly Ala
                 85                  90                  95
Gln Asn Leu Leu Val Pro Met Val Asp Thr Pro Ala Asp Ala Glu Ala
            100                 105                 110
Ala Val Arg Ser Val Tyr Tyr Pro Pro Arg Gly Val Arg Gly Val Gly
            115                 120                 125
Ser Ala Leu Ala Arg Ala Ser Arg Trp Asn Ala Val Pro Asn Tyr Leu
            130                 135                 140
Ala Arg Ala Glu Asp Phe Val Ser Leu Thr Ile Gln Ile Glu Ser Ala
145                 150                 155                 160
Thr Ala Val Asp Asn Ala Ala Glu Ile Ala Ala Val Asp Gly Val Asp
                165                 170                 175
Ala Val Phe Val Gly Pro Ser Asp Leu Ala Ala Ser Met Gly Leu Leu
            180                 185                 190
Gly Gln Gln Thr His Pro Asp Val Thr Asp Ala Val Leu Arg Thr Phe
            195                 200                 205
Asp Ala Val Lys Ala Ala Gly Lys Leu Val Gly Val Asn Ala Phe Asp
    210                 215                 220
Pro Asp Gln Ala Arg Lys Tyr Lys Asp Ala Gly Ala Ser Phe Val Leu
225                 230                 235                 240
Val Gly Ala Asp Val Gly Leu Met Met Asn Gly Ala Arg Ala Trp Ala
                245                 250                 255
Lys Thr Trp Val Gln Asp
                260
```

ALDOLASE AND PRODUCTION PROCESS OF 4-HYDROXY-L-ISOLEUCINE

This application is a continuation under 35 U.S.C. §120 of PCT Patent Application No. PCT/JP2007/056756, filed on Mar. 22, 2007, which claims priority under 35 U.S.C. §119(a) to Russian Patent Application No. 2006109216, filed on Mar. 24, 2006, the entireties of which are incorporated by reference. The Sequence Listing filed electronically herewith is also hereby incorporated by reference in its entirety (File Name: US-283_Seq_List; File Size: 27 KB; Date Created: Sep. 18, 2008).

BACKGROUND OF THE INVENTION

1. Field of the Invention

The present invention relates to the microbiological industry, and specifically to a novel aldolase and methods for manufacturing 4-hydroxy-L-isoleucine or a salt thereof.

2. Brief Description of the Related Art 4-hydroxy-L-isoleucine is an amino acid which can be extracted and purified from fenugreek seeds (*Trigonella foenum-graecum L. leguminosae*). 4-hydroxy-L-isoleucine displays an insulinotropic activity, which is of great interest because its stimulating effect is clearly dependent on the plasma glucose concentration in the medium, as demonstrated both in isolated perfused rat pancreas and human pancreatic islets (Sauvaire, Y. et al, Diabetes, 47: 206-210, (1998)). Such dependency on glucose has not been confirmed with sulfonylureas (Drucker, D. J., Diabetes 47: 159-169, (1998)), which are the only insulinotropic drug currently used to treat type II diabetes [or non-insulin-dependent diabetes (NIDD) mellitus (NIDDM)]. As a consequence, hypoglycemia remains a common undesirable side effect of sulfonylurea treatment (Jackson, J., and Bessler, R. Drugs, 22: 211-245; 295-320, (1981); Jennings, A. et al. Diabetes Care, 12: 203-208, (1989)). Methods for improving glucose tolerance (Am. J. Physiol. Endocrinol., Vol. 287, E463-E471, 2004) are also known. This glucometabolism enhancement activity, and its potential application to pharmaceuticals and health foods, has been reported (Japanese Patent Application Laid-Open No. Hei 6-157302).

Due to its particular insulinotropic action, 4-hydroxy-L-isoleucine, which is only found in plants, might be considered as a novel secretagogue for the treatment of type II diabetes. This is because Type II diabetes is characterized by defective insulin secretion associated with various degrees of insulin resistance (Broca, C. et al, Am. J. Physiol. 277 (Endocrinol. Metab. 40): E617-E623, (1999)).

A method of oxidizing iron, ascorbic acid, 2-oxyglutaric acid, and oxygen-dependent isoleucine by utilizing dioxygenase activity in fenugreek extract has been reported as a method for manufacturing 4-hydroxy-L-isoleucine (Phytochemistry, Vol. 44, No. 4, pp. 563-566, 1997). However, this method is unsatisfactory as a method of manufacturing 4-hydroxy-L-isoleucine because the activity of the enzyme is inhibited by the substrate at isoleucine concentrations of 20 mM and above, the enzyme has not been identified, the enzyme is derived from plant extracts and cannot be readily obtained in large quantities, and the enzyme is unstable.

An efficient eight-step synthesis of optically pure (2S,3R,4S)-4-hydroxyisoleucine with 39% overall yield has been disclosed. The key steps of this synthesis involve the biotransformation of ethyl 2-methylacetoacetate to ethyl (2S,3S)-2-methyl-3-hydroxy-butanoate with *Geotrichum candidum* and an asymmetric Strecker synthesis (Wang, Q. et al, Eur. J. Org. Chem., 834-839 (2002)).

A short six-step chemoenzymatic synthesis of (2S,3R,4S)-4-hydroxyisoleucine with total control of stereochemistry, the last step being the enzymatic resolution by hydrolysis of a N-phenylacetyl lactone derivative using the commercially available penicillin acylase G immobilized on Eupergit C(E-PAC), has also been disclosed (Rolland-Fulcrand, V. et al, J. Org. Chem., 873-877 (2004)).

But currently, there have been no reports of producing 4-hydroxy-L-isoleucine by enzymatic transamination of 4-hydroxy-3-methyl-2-keto-pentanoic acid or by any other enzymatic conversion from any other starting materials.

SUMMARY OF THE INVENTION

As a result of extensive research conducted in consideration of the aforementioned problems, the inventors of the present invention have found an aldolase that may be preferably used in the synthesis of the desired precursor of 4-hydroxy-L-isoleucine (free form and a salt form thereof, and may be referred to as "4HIL"; hereinafter the same). This precursor is 4-hydroxy-3-methyl-2-keto-pentanoic acid (free form and a salt form thereof, and may be referred to as "HMKP"; hereinafter the same), and is present in certain microbial species. It has also been found that 4-hydroxy-L-isoleucine is produced by combining the aldolase enzyme with an aminotransferase and/or dehydrogenase, thereby leading to completion of the present invention.

Aspects of the present invention include providing a novel aldolase and DNA encoding the aldolase, and a method for producing 4-hydroxy-L-isoleucine using the aldolase. The above objects were achieved by finding the novel aldolase of the present invention.

Therefore, it is an aspect of the present invention to provide a DNA selected from the group consisting of:

(a) A DNA comprising the nucleotide sequence of SEQ ID No: 1;

(b) A DNA that hybridizes under stringent conditions with a DNA having a nucleotide sequence complementary to the nucleotide sequence of SEQ ID No: 1 and encodes a protein having aldolase activity;

(c) A DNA that encodes a protein comprising the amino acid sequence of SEQ ID No: 2;

(d) A DNA that encodes a protein having the amino acid sequence of SEQ ID NO: 2, except that it contains a substitution, deletion, insertion, addition, or inversion of one or several amino acid residues and wherein the protein has aldolase activity; and (e) A DNA that encodes a protein having an amino acid sequence that is at least 70% homologous to the amino acid sequence of SEQ ID NO: 2 and wherein the protein has aldolase activity.

It is a further aspect of the present invention to provide a recombinant DNA comprising the DNA as described above and a vector DNA.

It a further aspect of the present invention to provide an isolated cell transformed with the recombinant DNA as described above.

It is still a further aspect of the present invention to provide a process for producing a protein having aldolase activity comprising cultivating the cell as described above in a medium, and accumulating a protein having aldolase activity in the medium, cells, or both.

Another aspect of the invention is to provide a protein selected from the group consisting of:

(f) a protein comprising the amino acid sequence of SEQ ID No: 2;

(g) a protein comprising the amino acid sequence of SEQ ID No: 2, except that it contains a substitution, deletion, insertion, addition, or inversion of one or several amino acid residues and wherein the protein has aldolase activity; and (h) a protein that is at least 70% homologous to the amino acid sequence of SEQ ID No: 2 and has aldolase activity.

It is a further aspect of the invention to provide a protein comprising:

(A) an activity that catalyze production of 4-hydroxy-3-methyl-2-keto-pentanoic acid from acetaldehyde and α-ketobutyric acid;

(B) an activity that is dependent on bivalent cations selected from the group consisting of $Zn^{2+}$, $Mn^{2+}$ and $Mg^{2+}$;

(C) a molecular weight of about 186 kDa as measured by gel filtration, and (D) a molecular weight per subunit of 27 kDa as measured by SDS-PAGE.

It is another aspect of the invention to provide a method for manufacturing 4-hydroxy-L-isoleucine or a salt thereof, comprising:

(1) reacting acetaldehyde and α-ketobutyric acid in an aqueous solvent in the presence of at least one aldolase selected from the group consisting of:

(a) a protein comprising the amino acid sequence of SEQ ID No: 2, (b) a protein comprising the amino acid sequence of SEQ ID No: 2, except that it contains a substitution, deletion, insertion, addition or inversion of one or several amino acid residues and wherein the protein has aldolase activity, and (c) a protein that is at least 70% homologous to the amino acid sequence of SEQ ID No: 2 and has aldolase activity;

(2) converting the produced 4-hydroxy-3-methyl-2-keto-pentanoic acid to 4-hydroxy-L-isoleucine; and (3) isolating the produced 4-hydroxy-L-isoleucine.

It is an aspect of the invention to provide the method as described above, wherein the 4-hydroxy-3-methyl-2-keto-pentanoic acid is converted to 4-hydroxy-L-isoleucine by an aminotransferase and/or a dehydrogenase, wherein the aminotransferase and/or dehydrogenase have a transamination activity in the presence of an amino group donor.

It is an aspect of the present invention to provide a method for manufacturing 4-hydroxy-L-isoleucine or a salt thereof, comprising:

(1) reacting acetaldehyde and α-ketobutyric acid in an aqueous solvent in the presence of a bacterium containing an aldolase selected from the group consisting of:

(a) a protein comprising the amino acid sequence of SEQ ID No: 2, (b) a protein comprising the amino acid sequence of SEQ ID No: 2, except that it contains a substitution, deletion, insertion, addition or inversion of one or several amino acid residues and wherein the protein has aldolase activity, and (c) a protein that is at least 70% homologous to the amino acid sequence of SEQ ID No: 2 and has aldolase activity, and wherein the aqueous solvent also contains an aminotransferase and/or a dehydrogenase which catalyzes conversion of 4-hydroxy-3-methyl-2-keto-pentanoic acid to 4-hydroxy-L-isoleucine in the presence of an amino group donor; and (2) isolating the produced 4-hydroxy-L-isoleucine.

It is an aspect of the invention to provide the method as described above, wherein the aminotransferase is a branched-chain amino acid aminotransferase.

It is an object of the invention to provide the method as described above, wherein the branched-chain amino acid aminotransferase is derived from a bacterium selected from the group consisting of *Escherichia* and *Bacillus*.

It is an aspect of the invention to provide the method as described above, wherein the amino group donor is selected from the group of L-amino acids.

It is an aspect of the invention to provide the method as described above, wherein the branched-chain amino acid aminotransferase is derived from a bacterium selected from the group consisting of *Escherichia* and *Bacillus*.

It is an aspect of the invention to provide the method as described above, wherein the bacterium has been modified to enhance at least one of the activities of the aldolase and the branched-chain amino acid aminotransferase.

It is an aspect of the invention to provide the method as described above, wherein the activities of the aldolase and the branched-chain amino acid aminotransferase are enhanced by increasing the expression of the aldolase and/or the branched-chain amino acid aminotransferase.

It is an aspect of the invention to provide the method as described above, wherein the expression of the aldolase and/or the branched-chain amino acid aminotransferase is increased by modifying an expression control sequence of the gene encoding the aldolase and/or branched-chain amino acid aminotransferase, or by increasing the copy number of the gene encoding the aldolase and/or branched-chain amino acid aminotransferase.

It is an aspect of the invention to provide the method as described above, wherein the bacterium belongs to the genus *Escherichia, Pseudomonas, Corynebacterium, Arthrobacter, Aspergillus* or *Bacillus*.

It is an aspect of the invention to provide the method as described above, wherein the bacterium belongs to *Escherichia coli, Arthrobacter simplex, Corynebacterium glutamicum, Arthrobactor globiformis, Arthrobactor sulfureus, Arthrobactor viscosus*, or *Bacillus subtilis*.

It is an aspect of the invention to provide the method as described above, wherein the bacterium is a bacterial culture, cells, or treated cells.

It is an aspect of the invention to provide the method as described above, wherein the 4-hydroxy-L-isoleucine is selected from the group consisting of (2S,3S,4S)-4-hydroxyisoleucine, (2S,3R,4R)-4-hydroxyisoleucine, (2S,3S,4R)-4-hydroxyisoleucine, (2S,3R,4S)-4-hydroxy-isoleucine, and combinations thereof.

BRIEF DESCRIPTION OF THE DRAWINGS

FIG. 4 shows structures of primers for PCR-amplification and sequencing of asiHPAL gene. A)—N-terminal sequence of HMKP aldolase from *Arthrobacter simplex* (NBRC 12069). B)—degenerative primer asiN10; I=deoxyinosine phosphate. C)—flanking primer SVS88.

FIG. 7 shows the alignment of asiHPAL and HHDE aldolase from *Brevibacterium linens* BL2.

DESCRIPTION OF THE PREFERRED EMBODIMENTS

Figure 1:
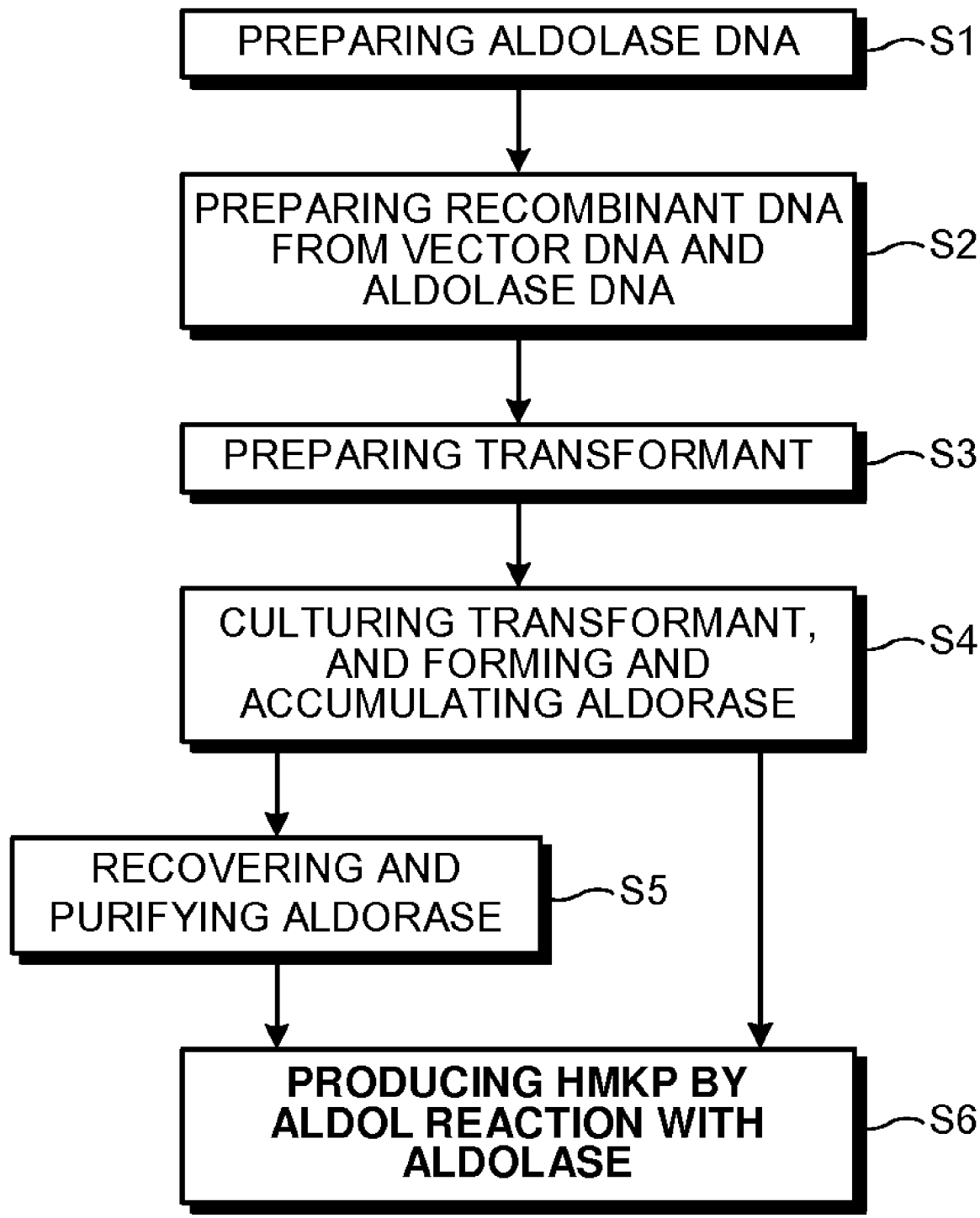
FIG. 1 shows a flowchart of the process for producing aldolase.

The term "4-hydroxy-L-isoleucine" or "4HIL" refers to a single compound or a diastereomer mixture of (2S,3S,4S)-4-hydroxyisoleucine, (2S,3R,4R)-4-hydroxyisoleucine, (2S,3S,4R)-4-hydroxy-isoleucine, and/or (2S,3R,4S)-4-hydroxyisoleucine, or any combination thereof.

The term "bacterium" includes enzyme-producing bacteria, a mutant and a genetic recombinant thereof in which the targeted enzymatic activity exists or has been enhanced, and the like.

The following provides a detailed explanation of [I] aldolase, [II] a process for producing 4-hydroxy-L-isoleucine using the aldolase with reference to the accompanying drawings.

[I] Aldolase

Bacterial strains were confirmed to contain aldolase having the ability to form 4-hydroxy-3-methyl-2-keto-pentanoic acid in the genus *Arthrobacter*.

It was found that *Arthrobacter simplex* possesses aldolase activity which can catalyze a reaction in which 4-hydroxy-3-methyl-2-keto-pentanoic acid is generated from acetaldehyde and α-ketobutyric acid (both the free form and a salt form thereof; hereinafter the same). The novel aldolase was purified and isolated from cultivated microbial cells.

Furthermore, the amino acid sequence of the aldolase was determined by purifying the native aldolase from *Arthrobacter simplex* AKU626 (NBRC12069) strain (hereinafter abbreviated as asiHPAL). Furthermore, a DNA molecule of about 30 base pairs deduced from the amino acid sequence of the aldolase was sequenced and isolated. The entire length of DNA that encodes asiHPAL was obtained by PCR using this DNA molecule.

The DNA encoding the asiHPAL is shown in SEQ ID No: 1. Furthermore, the amino acid sequence of asiHPAL encoded by the nucleotide sequence of SEQ ID No: 1 is shown in SEQ ID No: 2. SEQ ID No: 2 is the amino acid sequence of asiHPAL encoded by the nucleotide sequence of SEQ ID No: 1. AsiHPAL of SEQ ID No: 2 possesses the aldolase activity, and catalyzes the reaction in which 4-hydroxy-3-methyl-2-keto-pentanoic acid (HMKP) shown in the following formula (II) is synthesized from one molecule of acetaldehyde and one molecule of α-ketobutyric acid.

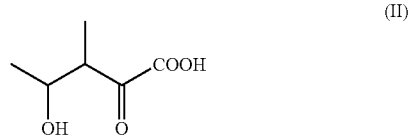

(II)

Next, a detailed explanation is provided of (1) the DNA encoding aldolase, (2) the properties of aldolase and (3) the process for producing aldolase, in that order.

(1) The DNA Encoding Aldolase

The aldolase gene having the nucleotide sequence of SEQ ID No: 1 was isolated from the chromosomal DNA of *Arthrobacter simplex* strain AKU626 (NBRC12069) as described in Example section. The amino acid sequence of SEQ ID No: 2 demonstrates homology of 55% with known HHDE-aldolase (2,4-dihydroxyhept-2-ene-1,7-dioic acid aldolase) (Submitted (08-APR-2005) National Center for Biotechnology Information, NIH, Bethesda, Md. 20894, USA) derived from *Brevibacterium linens* BL2 (FIG. 7).

Homology was calculated by using the "Vector NTI" genetic analytical software (Informax®, Invitrogen Life Science Software).

The following provides an explanation of the method for obtaining the DNA encoding aldolase from aldolase-producing bacteria.

First, a partial amino acid sequence of the purified aldolase is determined. At this time, a partial amino acid sequence (SEQ ID No: 3) of the aldolase derived from *Arthrobacter simplex* strain AKU626 (NBRC12069) was determined by using the automated degradation method of Edman (Edman, P., Acta Chem. Scand. 4, 227 (1950)) using the 491cLC Protein Sequencer (Applied Biosystems, USA The nucleotide sequence of a DNA that encodes this amino acid sequence is then able to be deduced based on the amino acid sequence. Universal codons are employed to deduce the nucleotide sequence of the DNA.

A DNA molecule of about 30 base pairs was then synthesized based on the deduced nucleotide sequence. The method used to synthesize the DNA molecule is disclosed in Tetrahedron Letters, 22, 1859 (1981). Furthermore, the DNA molecule may also be synthesized using the Synthesizer made by Applied Biosystems. The DNA molecule may be used as a probe to isolate the entire length of DNA that encodes aldolase from the chromosomal DNA library of a microorganism that produces aldolase. Alternatively, the DNA may also be used as a primer to amplify the DNA that encodes aldolase by PCR. However, since the DNA amplified by PCR may not contain the entire length of the aldolase DNA, the entire length of the DNA is isolated from a chromosomal DNA library of a microorganism that produces aldolase using the DNA amplified by PCR as a probe.

The procedure for PCR is described in publications such as White, T. J. et al., Trends Genet. 5, 185 (1989). The method for isolating a chromosomal DNA, as well as the method for isolating a desired DNA molecule from a gene library using a DNA molecule as a probe, are described in publications such as Molecular Cloning, 3rd edition, Cold Spring Harbor Laboratory Press (2001).

A method for determining the nucleotide sequence of an isolated DNA that encodes aldolase is described in A Practical Guide to Molecular Cloning, John Wiley & Sons, Inc. (1985). Furthermore, the nucleotide sequence may be determined by using the DNA Sequencer made by Applied Biosystems. A DNA encoding aldolase derived from *Arthrobacter simplex* strain AKU626 (NBRC12069) is shown in SEQ ID No: 1.

The DNA that encodes aldolase which catalyzes the reaction in which HMKP is formed from acetaldehyde and α-ketobutyric acid is not only the DNA shown in SEQ ID No: 1. This is because there may be differences in nucleotide sequences from each species and strain among *Arthrobacter* species.

Therefore, the DNA of the present invention not only includes the isolated DNA encoding aldolase, but also includes a DNA encoding aldolase in which mutations have been artificially induced as long as the DNA encodes aldolase which is still able to catalyze the above-mentioned reaction. Methods for artificially inducing mutations include commonly used methods such as introducing site-specific mutations, as described in Method. in Enzymol., 154 (1987).

A DNA that hybridizes under stringent conditions with a DNA which is complementary to the nucleotide sequence of SEQ ID No: 1, and encodes a protein having aldolase activity is also included in the DNA of the present invention. As used herein, the "stringent conditions" refer to those conditions under which a specific hybrid is formed and a non-specific hybrid is not formed. Although it is difficult to numerically express these conditions explicitly, by way of example, mention is made of those conditions under which DNA molecules having higher homology e.g. preferably 70% or more, more preferably 80% or more, still more preferably 90% or more, and particularly preferably 95% or more homology, hybridize with each other, while DNA molecules having lower homology do not hybridize with each other, or those conditions under which hybridization occurs under usual washing conditions in Southern hybridization, that is, at a salt concentration corresponding to 0.1×SSC and 0.1% SDS at 37° C., preferably 0.1×SSC and 0.1% SDS at 60° C., and more preferably 0.1×SSC and 0.1% SDS at 65° C. The length of the probe may be suitably selected, depending on the hybridization conditions, and usually varies from 100 bp to 1 kbp. Furthermore, "aldolase activity" means the synthesis of HMKP from acetaldehyde and α-ketobutyric acid. However, when a nucleotide sequence hybridizes under stringent conditions with a nucleotide sequence which is complementary to the nucleotide sequence of SEQ ID No: 1, the nucleotide sequence encodes an aldolase protein which preferably retains aldolase activity of 10% or more, preferably 30% or more, more preferably 50% or more, and still more preferably 70% or more, under conditions of 37° C. and pH 8.

Furthermore, a DNA encoding a protein which is substantially identical to the aldolase encoded by the DNA of SEQ ID No: 1 is also included in the DNA of the present invention. Namely, the following DNAs are also included in the DNA of the present invention:

(a) a DNA having the nucleotide sequence of SEQ ID No: 1;

(b) a DNA that hybridizes under stringent conditions with a DNA having a nucleotide sequence complementary to the nucleotide sequence of SEQ ID No: 1, and encodes a protein having aldolase activity;

(c) a DNA that encodes the protein having the amino acid sequence of SEQ ID No: 2;

(d) a DNA that encodes the protein having the amino acid sequence of SEQ ID NO: 2, except having substitutions, deletions, insertions, additions or inversions of one or several amino acid residues, wherein the protein maintains aldolase activity; and (e) a DNA that encodes a protein having an amino acid sequence that is at least 70% homologous, preferably at least 80% homologous, more preferably at least 90% homologous and still more preferably at least 95% homologous to the amino acid sequence of SEQ ID NO:2, and having the aldolase activity.

The phrase "one or several" refers to a range over which the 3-dimensional structure of a protein or aldolase activity is not significantly impaired, and more specifically, a range of 1 to 78, preferably 1 to 52, more preferably 1 to 26, and still more preferably 1 to 13, especially preferably 1 to 5.

The substitution, deletion, insertion, addition or inversion of one or several amino acid residues should be conservative mutation(s) so that the activity can be maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Furthermore, "aldolase activity" refers to the synthesis of HMKP from acetaldehyde and α-ketobutyric acid as described above. However, when the amino acid sequence contains a substitution, deletion, insertion, addition or inversion of one or several amino acid residues in the amino acid sequence of SEQ ID No: 2, this protein preferably retains aldolase activity of 10% or more, preferably 30% or more, more preferably 50% or more, and still more preferably 70% or more, of protein having the amino acid sequence of SEQ ID No: 2 under conditions of 37° C. and pH 8.

(2) Properties of Aldolase

Next, an explanation is provided of the properties of purified aldolase derived from *Arthrobacter simplex* strain AKU626 (NBRC12069) (asiHPAL).

asiHPAL has the amino acid sequence of SEQ ID No: 2 as was clearly determined by the previously described gene isolation and analysis. However, a protein having an amino acid sequence that contains a substitution, deletion, insertion, addition or inversion of one or several amino acid residues in the amino acid sequence of SEQ ID No: 2 is also included, and which also has aldolase activity.

Namely, the aldolase includes the following proteins:

(f) a protein having the amino acid sequence of SEQ ID No: 2;

(g) a protein having an amino acid sequence that contains a substitution, deletion, insertion, addition or inversion of one or a several amino acid residues in the amino acid sequence of SEQ ID No: 2, and having aldolase activity; and (h) a protein that is at least 70% homologous, preferably at least 80% homologous, more preferably at least 90% homologous and still more preferably at least 95% homologous to the amino acid sequence of SEQ ID NO:2, and having aldolase activity.

Here, the definitions of "several" and "aldolase activity" are the same as defined in section (1), DNA Encoding Aldolase.

The aldolase catalyzes the synthesis of 4-hydroxy-3-methyl-2-keto-pentanoic acid (HMKP) by aldol condensation reaction from acetaldehyde and α-ketobutyric acid.

The aldolase activity may be measured by determination of the HMKP formation from acetaldehyde and α-ketobutyric acid or the 4HIL formation after subsequent conversion from HMKP to 4HIL by using high-performance liquid chromatography (HPLC).

The aldolase is able to catalyze the synthesis of HMKP by aldol condensation reaction from acetaldehyde and α-ketobutyric acid. Two microbial enzymes capable of catalyzing the aldol condensation reaction using 2 molecules of α-keto acid (or substituted α-keto acid) as a substrate have been reported thus far. They are MhpE aldolase derived from *E. coli* (Appl. Environ. Microbiol., Vol. 64, No. 10, 4093-4094, 1998) and the aldolase reported by Sugiyama et al. (WO2004-018672). However, the quantities of HMKP produced were reported to be consistently less than 1 μM, which is not a sufficient amount for use in a further transamination process to produce 4-hydroxy-L-isoleucine. Therefore, there have been no findings or reports describing the production of HMKP with industrial applicability, and it is completely unknown as to whether it is possible to synthesize HMKP using this enzyme. Namely, the aldolase differs from aldolases that have been reported thus far in that it is able to catalyze the synthesis of HMKP by aldol condensation of acetaldehyde and α-ketobutyric acid.

Next, the following is a description of the enzymatic properties for purified asiHPAL.

asiHPAL catalyzes the formation of HMKP, which is represented by the following general formula (II):

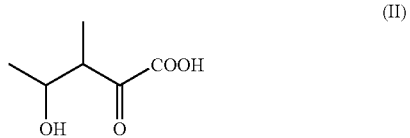

(II)

from acetaldehyde and α-ketobutyric acid. Thus, the process of producing HMKP from acetaldehyde and α-ketobutyric acid using asiHPAL is also described herein.

Furthermore, the activity of asiHPAL strictly depends on $Zn^{2+}$, $Mg^{2+}$ and $Mn^{2+}$ ions, and is completely blocked in the presence of EDTA. So, asiHPAL may belong to the Type II aldolases (see Table 3).

Since the molecular weight of asiHPAL is about 186 kDa as measured by gel filtration and about 27 kDa as measured by SDS-PAGE, asiHPAL might have a hexameric structure.

Therefore, the protein is also defined by following characteristics:

(A) has an activity of catalyzing production of 4-hydroxy-3-methyl-2-keto-pentanoic acid from acetaldehyde and α-ketobutyric acid;

(B) the activity is dependent on one or more bivalent cations, including $Zn^{2+}$, $Mn^{2+}$ and $Mg^{2+}$; and (C) the molecular weight as measured by gel filtration is about 186 kDa, and the molecular weight per subunit as measured by SDS-PAGE is about 27 kDa.

(3) Process for Producing Aldolase

Next, the process of producing the aldolase is described. There are two ways to produce the aldolase: (i) cultivating an aldolase-producing microorganism to produce aldolase, and (ii) preparing a transformant by recombinant DNA technology and cultivating the transformant to produce aldolase.

(i) Process for Producing Aldolase by Microbial Cultivation

Microorganisms which are sources of native aldolase include microorganisms belonging to the genus *Arthrobacter*.

Any microorganisms belonging to the genus *Arthrobacter* may be used provided they are microorganisms that produce aldolase which catalyzes the synthesis of a precursor keto acid (HMKP) from acetaldehyde and α-ketobutyric acid. Preferably, these microorganisms include *Arthrobacter simplex* (AKU626, NBRC12069), *Arthrobacter globiformis* (AKU625 strain, NBRC12140 strain), *Arthrobacter sulfureus* (AKU635 strain, NBRC12678 strain) and *Arthrobactor viscosus* (AKU636 strain, NBRC13497 strain). Among these, *Arthrobacter simplex* (AKU626, NBRC12069) is particularly preferable. The particulars on the deposits of these microorganisms are indicated below.

Of the above bacteria, those strains the designation of which begins with AKU may be obtained from the Laboratory of Fermentation Physiology and Applied Microbiology, Division of Applied Life Sciences, Faculty of Agriculture, Graduate School, Kyoto University.

Those strains the designation of which begins with NBRC (formerly IFO) can be obtained from the National Institute of Technology and Evaluation (2-5-8 Kazusakamatari, Kisarazu-shi, Chiba, Postal Code 292-0818). The registration numbers of individual strains are recorded in the NBRC catalog:

(http://www.nbrc.nite.go.jp/NBRC2/NBRCDispSearchServlet?lang=en).

Although the microorganism may be cultivated either as liquid cultivation and/or solid cultivation, an industrially advantageous method is the deep-aerated stir cultivation. Carbon sources, nitrogen sources, inorganic salts, and other trace nutrient elements commonly used in microbial cultivating may be used in the media. Any nutrient source may be used so long it is usable by the chosen microbial strain.

Culturing is conducted under aerobic conditions by shake culturing, deep ventilation stir culturing, or the like. The temperature may be within a range in which the microorganisms grow and aldolase is produced. Thus, although the conditions are not strict, the temperature is normally 10 to 50° C. and preferably 15 to 42° C. The cultivating time varies according to other cultivating conditions. For example, the microorganisms may be cultivated until the greatest amount of aldolase is produced, and this is normally about 5 hours to 7 days, and preferably about 10 hours to 96 hours.

Following cultivation, the microbial cells are recovered by centrifugation (e.g., 10,000×g for 10 minutes). Since the majority of the aldolase is present in the cells, the aldolase is solubilized by disrupting or lysing the microbial cells. Ultrasonic disruption, French press disruption, or glass bead disruption may be used to disrupt the microbial cells. When lysing the cells, egg white lysozyme, peptidase treatment, or a suitable combination thereof may be used.

When aldolase is purified from an aldolase-producing microorganism, although an enzyme solubilizing solution is used, if undisrupted or unlysed residue or debris remains, re-centrifuging the solubilization solution and removing any residue or debris that precipitates is advantageous to purification.

All commonly used methods for purifying typical enzymes may be employed to purify the aldolase, examples of which include ammonium sulfate precipitation, gel filtration chromatography, ion exchange chromatography, hydrophobic interaction chromatography and hydroxyapatite chromatography. As a result, an aldolase-containing fraction with higher specific activity may be obtained.

(ii) Production Process Using Recombinant DNA Technology

Next, the process for producing aldolase using a recombinant DNA technology is described. There are numerous known examples of producing useful proteins such as enzymes and physiologically active substances using recombinant DNA technology. This technology enables mass production of useful proteins which are present only in trace amounts in nature.

FIG. 1 is a flowchart of the process for producing the aldolase of the present invention.

First, a DNA is prepared that encodes the aldolase of the present invention (Step S1).

Next, the DNA is ligated with a vector DNA to produce a recombinant DNA (Step S2), and cells are transformed with this recombinant DNA to produce a transformant (Step S3). Then, the transformant is cultivated in a medium, and the aldolase is produced, and accumulates in the medium, cells, or both (Step S4).

Subsequently, the process proceeds to Step S5 where the aldolase is recovered and purified.

Large amounts of HMKP may be produced by using the purified aldolase produced at Step S5, or the medium and/or the cells in which containing the aldolase (Step S4), in an aldol condensation reaction (Step S6).

The vector DNA ligated with the aldolase gene allows for expression of the aldolase of the present invention.

Aldolase genes which are ligated into the vector DNA include the previously described DNA as in [I].

When using recombinant DNA technology for large scale production of proteins, cells such as bacterial cells, *Actinomyces* cells, yeast cells, mold cells, plant cells, and animal cells may be used as host cells. Examples of bacterial cells for which host-vector systems have been developed include *Escherichia* species, *Pseudomonas* species, *Arthrobacter* species, *Corynebacterium* species, *Aspergillus* species, and *Bacillus* species. *Escherichia coli* or *Corynebacterium glutamicum* are preferably used in the present invention. This is because there is much known regarding mass production of proteins using *Escherichia coli* or *Corynebacterium glutamicum*. The following describes the process for producing aldolase using a transformed *E. coli*.

A promoter which is typically used for heterogeneous protein production in *E. coli* may be used to express the DNA encoding aldolase. Powerful promoters include the T7 promoter, trp promoter, lac promoter, tac promoter, and PL promoter.

To produce aldolase as a fused protein, a gene that encodes another protein, preferably a hydrophilic peptide, is ligated either upstream or downstream of the aldolase gene. The gene that encodes the other protein may function to increase the amount of the fused protein which is produced, and/or enhance the solubility of the fused protein after the denaturation and regeneration steps. The T7 gene 10, β-galactosidase gene, dihydrofolate reductase gene, interferon-γ gene, interleukin-2 gene, polyhistidine gene, glutathione S-transferase gene, and prochymosin gene are examples of the gene which can be fused to the aldolase gene.

When ligating to the aldolase gene, the codon reading frames must match. The genes may either be ligated in a suitable restriction enzyme site or using a synthetic DNA of an appropriate sequence.

In order to increase the amount produced, it is preferable to couple a transcription terminating sequence, such as a terminator, downstream from the fused protein gene. The T7 terminator, fd phage terminator, T4 terminator, tetracycline resistance gene terminator, and *E. coli* trpA gene terminator may be used.

Multi-copy vectors are preferable to introduce a gene that encodes aldolase or a fused protein of aldolase into *E. coli*. Plasmids with a replication starting point derived from Col E1 such as pUC plasmids, pBR322 plasmids, or their derivatives may be used. A "derivative" here refers to a plasmid that has a base alteration such as a substitution, deletion, insertion, addition, or inversion. These alteration may include those caused by mutagenic treatment using a mutagen or UV, spontaneous mutations, or random mutations.

It is preferable that the vector has a marker such as an ampicillin resistance gene so that the transformant may be easily selected. Examples of such plasmids include commercially available expression vectors having a powerful promoter (such as pUC (Takara), pPROK (Clontech), and pKK233-2 (Clontech)).

The recombinant DNA is obtained by ligating the chosen promoter, the gene encoding aldolase or the fused protein of aldolase and another protein, and the terminator in that order, with a vector DNA.

When *E. coli* is transformed with the recombinant DNA and then cultivated, aldolase or the fused protein of aldolase with another protein is expressed and produced. A strain that is typically used for expression of heterogeneous genes may be used as the transformed host, and *E. coli* strain JM109 (DE3) and *E. coli* strain JM109 are particularly preferable. The transformation method and method for selecting the transformant are described in, for example, Molecular Cloning, 3rd edition, Cold Spring Harbor Laboratory Press (2001).

When expressing the fused protein, the aldolase may be cut out using a restriction protease, such as blood coagulation factor Xa or kallikrein. These proteases recognize sequences which are not present in aldolase.

A medium which is typically used for cultivating *E. coli* may be used as the production medium. Examples include M9-casamino acid medium and LB medium. Furthermore, conditions for cultivating and inducing production may be appropriately selected depending the type of the marker and promoter which is used, as well as the type of host microorganism.

The following method may be used to recover the aldolase or fused protein. If the aldolase or the fused protein is solubilized within the microbial cells, then the crude enzyme solution may be used after disrupting or lysing the recovered cells. Furthermore, the aldolase or the fused protein may also be purified by precipitation, filtration, column chromatography, or other common techniques, as necessary. An antibody of the aldolase or its fused protein may also be used for purification.

When a protein inclusion body forms, it may be solubilized with a denaturant. Although it may be solubilized with microbial cell protein, in consideration of the subsequent purification procedure, it is preferable to take out the inclusion body and then solubilize it. A method known in the prior art may be used to recover the inclusion body from the microbial cell. For example, the inclusion body may be recovered by disrupting the microbial cell, followed by centrifugal separation. Examples of denaturants that solubilize protein inclusion bodies include guanidine hydrochloride (e.g., 6 M, pH 5-8) and urea (e.g., 8 M).

The protein inclusion body may be regenerated as an active protein by removing these denaturants by a treatment such as dialysis. Dialysis solutions such as Tris-HCl buffer or phosphate buffer may be used for dialysis, and the concentration may be from 20 mM to 0.5 M, and the pH may be from pH 5 to pH 8.

The protein concentration during the regeneration step is preferably maintained at about 500 µg/ml or less. In order to prevent the regenerated aldolase from crosslinking to itself, the dialysis temperature is preferably 5° C. or lower. Furthermore, the activity may be restored by removing the denaturant by dilution and ultrafiltration, in addition to dialysis.

When the aldolase gene is derived from bacteria belonging to the genus *Arthrobacter*, the aldolase may be expressed and produced using the *Arthrobacter* species bacteria as a host. Examples of such host cells and recombinant expression systems used therein include a recombinant expression method in *Arthrobacter* sp. (Shaw P. C. et al., J Gen Micobiol. 134 (1988) p. 903-911), a recombinant expression method in *Arthrobacter nicotinovorans* (Sandu C. et al., Appl Environ Microbiol. 71 (2005) p 8920-8924), and a recombinant expression method in *Arthrobacter* sp. (Morikawa, M. et al., Appl Microbiol Biotechnol., 42 (1994), p. 300-303). Also, expression systems developed for Coryneform bacteria are also applicable in *Arthrobacter* species (Sandu C. et al.). However, the present invention is not limited to the *Arthrobacter* species bacteria expression system for aldolase as described herein.

[II] Method for Producing 4-hydroxy-L-isoleucine

The method for producing 4-hydroxy-L-isoleucine (4HIL) of the present invention is a two step reaction: (1) enzymatic aldol condensation reaction to produce 4-hydroxy-3-methyl-2-keto-pentanoic acid (HMKP) from acetaldehyde and α-ketobutyric acid (reaction formula (III) below), and (2) conversion from HMKP to 4HIL, that is, enzymatic transamination producing 4HIL from HMKP (reaction formula (IV) below). These steps may be continuously performed in this order or almost simultaneously performed in one container. Each step is described below.

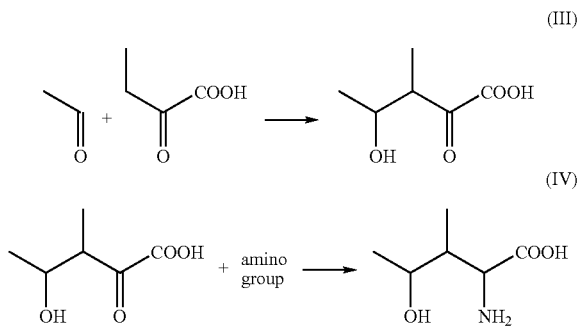

(1) Producing 4-hydroxy-3-methyl-2-keto-pentanoic Acid (HMKP)

HMKP (II) is produced by reacting acetaldehyde and α-ketobutyric acid:

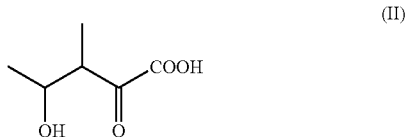

wherein the reaction is performed in the presence of an aldolase that catalyzes the reaction.

There are no particular limitations on the aldolase that is used to catalyze the reaction, and any protein may be used as long as the protein is capable of catalyzing the synthesis of HMKP represented by the general formula (II) by aldol condensation of acetaldehyde and α-ketobutyric acid.

A preferable example of such an aldolase is the aldolase described in section [1]. Aldolase may be used in any form, such as in a bacterium (including a culture, bacterial cells, or treated cells), a purified enzyme, or a crude enzyme, so long as it is able to catalyze the production of HMKP. When a bacterium is used as the source of the aldolase, both a bacterium which naturally produces the aldolase, such as microorganisms belonging to the genus *Arthrobacter*, and a recombinant microorganism which has been transformed with a recombinant DNA as described in section [1] are encompassed.

For example, when producing HMKP using an aldolase-producing bacterium or bacterial cells that have been transformed with a recombinant DNA, the substrate may be added directly to the culture media during cultivation, or the substrate may be bacterial cells or washed bacterial cells that have been separated from the culture. Furthermore, bacterial cells that have been disrupted or lysed may be used directly, or the aldolase may be recovered from the treated bacterial cells and used as a crude enzyme solution, or a purified enzyme may be used. Namely, as long as aldolase activity is present, the aldolase-activity containing fraction may be used in the process for producing a 4HIL of the present invention.

The aldol condensation reaction is performed in a reaction solution containing acetaldehyde, α-ketobutyric acid, and aldolase or aldolase-containing composition, adjusted to a suitable temperature of 20 to 50° C., and allowing to stand undisturbed, shaking or stirring for 30 minutes to 5 days while maintaining at pH 5 to 12.

The speed of the reaction may also be increased by adding a bivalent cation such as $Mg^{2+}$, $Mn^{2+}$, $Fe^{2+}$, $Zn^{2+}$ or $Co^{2+}$ to the reaction mixture. $Zn^{2+}$ may be used preferably in terms of cost and so forth.

When adding these bivalent cations to the reaction solution, although any salt may be used provided it does not hinder the reaction, $ZnCl_2$, $ZnSO_4$, $MgSO_4$, and so forth may be used preferably. The concentrations of these bivalent cations may be suitably determined by simple preliminary studies. These bivalent cations may be added within the range of 0.01 mM to 10 mM, preferably 0.11 mM to 5 mM.

The HMKP may be either separated or purified according to known techniques, or not, particularly when produced by a recombinant microorganism which expresses both aldolase and aminotransferase. Separation and purification methods include contacting the HMKP with an ion exchange resin to adsorb basic amino acids, followed by elution and crystallization. Another purification method includes when the elution product is discolored and filtration with activated charcoal is necessary, then crystallization can be performed to obtain HMKP.

The process for producing HMKP makes it possible to form a precursor keto acid (HMKP) of 4-hydroxy-L-isoleucine (4HIL) from acetaldehyde and α-ketobutyric acid. Since HMKP may be used to derive 4-hydroxy-L-isoleucine by amination at position 2, it is useful as an intermediate in 4-hydroxy-L-isoleucine synthesis. The process for producing 4-hydroxy-L-isoleucine from HMKP is described next.

(2) Converting 4-hydroxy-3-methyl-2-keto-pentanoic Acid to 4-hydroxy-L-isoleucine Once HMKP is produced as described above (1), HMKP is converted to 4HIL.

Methods for converting HMKP to 4HIL are not particularly limited, and either chemical or enzymatic methods may be used. As for enzymatic conversion, enzymatic transamination is preferable. In this step, "transamination" means the reaction whereby an amino group is transferred from a donor compound, for example, L-glutamic acid or L-glutamate, to an acceptor compound with a keto-group, for example, 4-hydroxy-3-methyl-2-keto-pentanoic acid or the like. Although the amino group donor is not particularly limited as long as it has an amino group, L-amino acids such as L-glutamic acid and branched-chain amino acids are preferably used.

In the present invention, "enzymatic transamination" means a transamination reaction which is carried out by an aminotransferase (transaminase) or a dehydrogenase enzyme. Particularly a bacterial aminotransferase (transaminase) is preferred. These enzymes may be used in any form, such as in a bacterium (including a culture, bacterial cells, or treated cells), a purified enzyme, or a crude enzyme, so long as it incorporates the above aminotransferase and/or dehydrogenase. To reduce the cost for producing 4HIL by simplifying the process, adding the substrate directly to the culture solution is most preferable.

The aminotransferase and/or dehydrogenase used in this step is not particularly limited as long as HMKP can be converted to 4HIL. A branched-chain amino acid aminotransferase (BCAT) is preferable. For example, the aminotransferase encoded by the ilvE gene, the aromatic aminotransferase encoded by tyrB gene, the aspartate aminotransferase encoded by aspC gene, the valine-pyruvate aminotransferase encoded by avtA gene in *E. coli*, the aminotransferase encoded by ywaA gene in *Bacillus subtilis*, and the like are exemplified An exemplary protein sequence of BCAT is COG0115 (SEQ ID NO: 13). Also, the protein belonging to BCAT is shown as EC 2.6.1.42.

Practically all branched-chain amino acid aminotransferases exhibit broad substrate specificity, so most of them can use HMKP as a substrate for the amino-group transfer.

The branched-chain amino acid aminotransferase catalyzes the transfer of an amino-group from L-glutamic acid to different α-keto acids, such as α-keto-isovaleric acid, 2-keto-3-methylvaleric acid, and 2-keto-4-methylpentanoic acid, resulting in formation of L-valine, L-isoleucine, and L-leucine, respectively.

The branched-chain amino acid aminotransferases from a great majority of microorganisms are known, and the nucleotide sequences of genes encoding these aminotransferases have also been disclosed.

The ilvE gene encodes the IlvE protein, which is a branched-chain amino acid aminotransferase from *Escherichia coli*, (synonyms include B3770, IlvE, branched-chain amino acid: 2-oxoglutaric acid aminotransferase, BCAT, transaminase B, leucine transaminase, valine transaminase, and isoleucine transaminase). This branched-chain amino acid aminotransferase may be abbreviated as ecoBCAT. The ilvE gene is located between the ilvM and ilvD genes on the chromosome of *E. coli* strain K-12. The nucleotide sequence of the ilvE gene is known (nucleotide positions: 3950507 to 3951436; GenBank accession no. NC_000913.2; gi:49175990) (SEQ ID NO: 14). The nucleotide sequence of the ilvE gene and the amino acid sequence of the IlvE protein encoded by the ilvE gene are shown in SEQ ID NO: 14 and SEQ ID NO: 15, respectively.

The ywaA gene encodes the branched-chain amino acid aminotransferase from *Bacillus subtilis*. This branched-chain amino acid aminotransferase may be abbreviated as bsuB-CAT. The ywaA gene is located between the dltE and licH genes on the chromosome of *B. subtilis* strain 168. The nucleotide sequence of the ywaA gene is known (nucleotide positions: 3956412 to 3957503; GenBank accession no. NC_000964.2; gi:50812173) (SEQ ID NO: 16). The nucleotide sequence of the ywaA gene and the amino acid sequence of the YwaA protein encoded by the ywaA gene are shown in SEQ ID NO: 16 and SEQ ID NO:17, respectively.

Other genes encoding branched-chain amino acid aminotransferases from other microorganisms can be identified by homology to known genes encoding branched-chain amino acid aminotransferases, followed by evaluation of the activity of the proteins encoded by the genes.

Homology between two amino acid sequences can be determined using well-known methods, for example, the computer program BLAST 2.0, which calculates three parameters: score, identity, and similarity.

Therefore, the ilvE gene from *E. coli* and ywaA gene from *B. subtilis* can be obtained by PCR (polymerase chain reaction; refer to White, T. J. et al., Trends Genet., 5, 185 (1989)) utilizing primers based on the known nucleotide sequence of the gene. Genes encoding branched-chain amino acid aminotransferases from other microorganisms can be obtained in a similar manner.

Since there may be some differences in DNA sequences between bacterial strains, the above-described genes encoding aldolase or BCAT are not limited to the nucleotide sequences shown in SEQ ID NOS: 1, 14 and 16 but may also include nucleotide sequences similar to those shown in SEQ ID NOS: 1, 14 and 16. Therefore, the protein variants encoded by the above-described genes may have a homology of not less than 70%, preferably not less than 80%, more preferably not less than 90%, and most preferably not less than 95%, with respect to the entire amino acid sequences shown in SEQ ID NOS. 2, 15 and 17, as long as the proteins are able to catalyze the reactions.

Moreover, the above-described genes may be represented by variants which can hybridize under stringent conditions with the nucleotide sequences shown in SEQ ID NOS: 1, 14 and 16 or with probes prepared based on these nucleotide sequences, provided that they encode functional proteins. "Stringent conditions" used here is the same as aforementioned section, [1]

(1) A DNA Encoding Aldolase.

The treated bacterial cells may be in the form of dried bacterial mass, freeze-dried bacterial mass, products treated with surfactants or organic solvents, enzyme-treated products, ultrasound-treated products, mechanically ground products, solvent-treated products, protein fractions of bacterial mass, immobilized products of bacterial mass, and processed bacterial mass.

Production of 4HIL from HMKP by transamination may be continuously performed after the aldol reaction, subsequent separation and/or purification of produced HMKP; or it may be simultaneously performed in the same reaction solution by allowing the aldolase and the aminotransferase to coexist. When the reactions are performed in the same reaction solution (one pot reaction), the aldolase and the aminotransferase may be co-expressed in a bacterium. Or these enzymes may be prepared separately as described above and added into the reaction solution. A bacterium (host cell) that co-expresses the DNA encoding aldolase and the DNA encoding aminotransferase may be prepared by co-transfection with the expression vectors each containing the aldolase and aminotransferase DNAs, or transformation with the expression vector which contains both the aldolase and aminotransferase DNA in a form capable of expression in the host cell. Furthermore, increasing the expression of the genes encoding aldolase and the branched-chain amino acid aminotransferase is the preferable method for enhancing the activities of the aldolase and the aminotransferase.

The phrase "increasing the expression of the gene" means that the expression of the gene is higher than that of a non-modified strain, for example, a wild-type strain. Examples of such modifications include increasing the copy number of expressed gene(s) per cell, increasing the expression level of the gene(s), and so forth. The copy number of an expressed gene can be measured, for example, by restricting the chromosomal DNA followed by Southern blotting using a probe based on the gene sequence, fluorescence in situ hybridization (FISH), and the like. The level of gene expression can be measured by various known methods including Northern blotting, quantitative RT-PCR, and the like. The amount of the expressed protein can be measured by known methods including SDS-PAGE followed by immunoblotting assay (Western blotting analysis), and the like.

"Transformation of a bacterium with DNA encoding a protein" means introducing the DNA into a bacterium, for example, by conventional methods. Transformation of this DNA will result in an increase in expression of the gene encoding the protein, and will enhance the activity of the protein in the bacterial cells. Methods of transformation include any known methods that have hitherto been reported. For example, treating recipient cells with calcium chloride so as to increase permeability of the cells to DNA has been reported for *Escherichia coli* K-12 (Mandel, M. and Higa, A., J. Mol. Biol., 53, 159 (1970)) and may be used.

Methods of enhancing gene expression include increasing the gene copy number. Introducing a gene into a vector that is able to function in the bacterium increases the copy number of the gene. For such purposes, multi-copy vectors can be preferably used. The multi-copy vector is exemplified by pBR322, pMW119, pUC19, pET22b, or the like.

Enhancing gene expression may also be achieved by introducing multiple copies of the gene into the bacterial chromosome by, for example, homologous recombination, Mu integration, or the like. For example, one act of Mu integration allows for up to 3 copies of the gene to be introduced into the bacterial chromosome.

Increasing the copy number of the gene can also be achieved by introducing multiple copies of the gene into the chromosomal DNA of the bacterium. In order to introduce multiple copies of the gene into a bacterial chromosome, homologous recombination is carried out using a sequence which is present in multiple copies as targets in the chromosomal DNA. Sequences having multiple copies in the chromosomal DNA include, but are not limited to repetitive DNA, or inverted repeats present at the end of a transposable element. Also, as disclosed in U.S. Pat. No. 5,595,889, it is possible to incorporate the gene into a transposon, and transfer it to introduce multiple copies of the gene into the chromosomal DNA.

Enhancing gene expression may also be achieved by placing the DNA under the control of a potent promoter. For example, the Ptac promoter, the lac promoter, the trp promoter, the trc promoter, the PR, or the PL promoter of lambda phage are all known to be potent promoters. The use of a potent promoter can be combined with multiplication of gene copies.

Alternatively, the effect of a promoter can be enhanced by, for example, introducing a mutation into the promoter to increase the transcription level of a gene located downstream of the promoter. Furthermore, it is known that substitution of several nucleotides in the spacer region between the ribosome binding site (RBS) and the start codon, especially the sequences immediately upstream of the start codon, profoundly affect the mRNA translatability. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Previously, it was shown that the rhtA23 mutation is an A-for-G substitution at the −1 position relative to the ATG start codon (ABSTRACTS of 17th International Congress of Biochemistry and Molecular Biology in conjugation with 1997 Annual Meeting of the American Society for Biochemistry and Molecular Biology, San Francisco, Calif. Aug. 24-29, 1997, abstract No. 457).

Moreover, it is also possible to introduce a nucleotide substitution into the promoter region of the gene on the bacterial chromosome, which results in stronger promoter function. The alteration of the expression control sequence can be performed, for example, in the same manner as the gene substitution using a temperature-sensitive plasmid, as disclosed in International Patent Publication WO 00/18935 and Japanese Patent Application Laid-Open No. 1-215280.

Methods for the preparation of plasmid DNA include, but are not limited to digestion and ligation of DNA, transformation, selection of an oligonucleotide as a primer, and the like, or other methods well known to one skilled in the art. These methods are described, for instance, in "Molecular Cloning A Laboratory Manual, Third Edition", Cold Spring Harbor Laboratory Press (2001).

EXAMPLES

The present invention will be explained in further detail with reference to the following non-limiting examples.

Example 1

Purification of asiHPAL

The purification protocol includes the following procedures.

Step1: 1 ml of overnight bacterial culture (grown for 12 h at 34° C.) of *Arthrobacter simplex* AKU626 was used to inoculate 5 liters of LB-broth [8×(375 ml in 1 L flask)]. Cells were cultivated at an optimal temperature for about 24 hours. Then, cells were harvested by centrifugation (16000×g) at 4° C., and re-suspended in 30 ml of buffer A [50 mM $KH_2PO_4$ (pH 7.4 adjusted by KOH)] supplemented by 1 mM PMSF (phenylmethylsulfonyl fluoride).

Step2: Cells were disrupted by 3-5 passages through a French pressure cell (max P=2.5 Psi) followed by centrifugation to remove debris. Protein preparation was passed through Sephadex G-15 column (2.6×28 cm) equilibrated with buffer A.

Step3: Anion-exchange chromatography (AEC 1) was carried out using ÄKTAbasic100 system supplemented with 50 ml DEAE (fast flow) column (d=1.6 cm). 40-50 ml of the protein preparation obtained from Step2 were applied to a column equilibrated with buffer A. The elution was performed at a flow rate of 2.5 ml/min with a liner gradient of 0-0.5 M NaCl in buffer A (10 CV (column volumes)). Each 10 ml-fraction was collected. Active fractions were pooled and desalted as described in "step2" item.

Step4: Anion-exchange FPLC (AEC 2) was carried out using the ÄKTAbasic100 system, and supplemented with an 1.6 ml "Sourse15Q" column (Amersham Pharmacia Biotech). The protein preparation obtained from Step3 was applied to column equilibrated with buffer A. The elution was carried out at flow rate 1 ml/min by liner 0-0.5 M NaCl in buffer A (40 CV). 2 ml fractions were collected. Active fractions were pooled (Tables 1, 2).

Step5: Hydrophobic interaction chromatography (HIC) was carried out using the ÄKTAbasic100 system, and supplemented with an 1 ml "Resource PHE" column (Amersham Pharmacia Biotech). The protein concentration in the preparation obtained from Step 5 was adjusted to 0.8 mg/ml and then ammonium sulphate was added up to final concentration 1.5 M. The protein solution was applied to a column equilibrated with buffer A, and supplemented with 1.5 M ammonium sulfate. Elution was performed at flow rate of 1 Ml/min with a liner gradient from 1.5 M to 0 M ammonium sulfate in buffer A (30 CV). 1 ml fractions were collected. Active fractions were pooled (Tables 1, 2).

TABLE 1

Purification of the asiHPAL.

| Step | Volume (ml) | Protein conc. (mg/ml) | Total protein (mg) | Specific [1] activity (nmoles/mg/min) | Total Activity [2] (nmoles/min) | Yield % [3] | Purification rate [4] |
|---|---|---|---|---|---|---|---|
| Lysate | 120 | 12.6 | 1512 | 0.6 | 903 | 100.00 | 1 |
| AEC1 | 20 | 0.7 | 14 | 30 | 401 | 45 | 48 |
| AEC2 | 4 | 1 | 4 | 100 | 402 | 45 | 167 |
| HIC | 1 | 0.1 | 0.1 | 1419 | 142 | 16 | 2365 |
| SEC | 1 | 0.04 | 0.04 | 1490 | 60 | 7 | 2483 |

[1] Specific activity was determined by monitoring via HPLC of the time-dependent 4HIL formation in the bsuBCAT/asiHPAL bi-enzymatic reaction with the following composition [100 mM L-glutamate (pH 8 ajusted by pH 8.0), 100 mM α-ketobutyrate, 100 mM acetaldehyde], 1 mM $ZnCl_2$, and 0.5 μg purified bsuBCAT) and an aliquot of the active fraction of asiHPAL was separated. All reactions were carried out at 37° C.
[2] Calculated as (Total protein) × (Specific activity).
[3] Calculated as 100% × (Total activity/Total activity in crude lysate).
[4] Calculated as (Specific activity/Specific activity in crude cell lysate).

TABLE 2

Chromatographic elution parameters. [a] Chromatographic stages.

| AEC 1 NaCl, M | AEC 2 NaCl, M | HIC $(NH_4)_2SO_4$, M | SEC $V_e/V_o$ |
|---|---|---|---|
| 0.35-0.37 | 0.31-0.35 | 0.19-0.1 | 1.5 |

[a] Data are presented as a salts concentration interval within HPAL activity eluted Step6: Size exclusion chromatography (SEC) was performed using the ÄKTAbasic100 system, and supplemented with a Superdex™ 200 HR 10/30A (Amersham Pharmacia Biotech) column. The protein preparation obtained from Step5 was applied to a column equilibrated with buffer A, and supplemented with 100 mM NaCl. Isocratic elution occurred at a flow rate of 0.5 ml/min. 1 ml fractions were collected. Active fractions were pooled (Tables 1, 2; FIG. 1).

The specific activity of asiHPAL was determined by HPLC monitoring of the time-dependent 4HIL formation in the bsuYwaA/asiHPAL bi-enzymatic reaction with following composition [100 mM L-glutamate (pH 8 adjusted by pH 8.0), 100 mM α-ketobutyrate, 100 mM acetaldehyde], 1 mM $ZnCl_2$, and 0.5 μg purified His-tag-bsuBCAT protein (branched-chain amino acid aminotransferase from *Bacillus subtilis*) and an aliquot of the elution fraction. All reactions were carried out at 37° C. Cloning the branched-chain amino acid aminotransferase from *Bacillus subtilis* (bsuBCAT) and HPLC measuring the 4HIL formation are described in the Examples 5 and 6, respectively.

Figure 2:
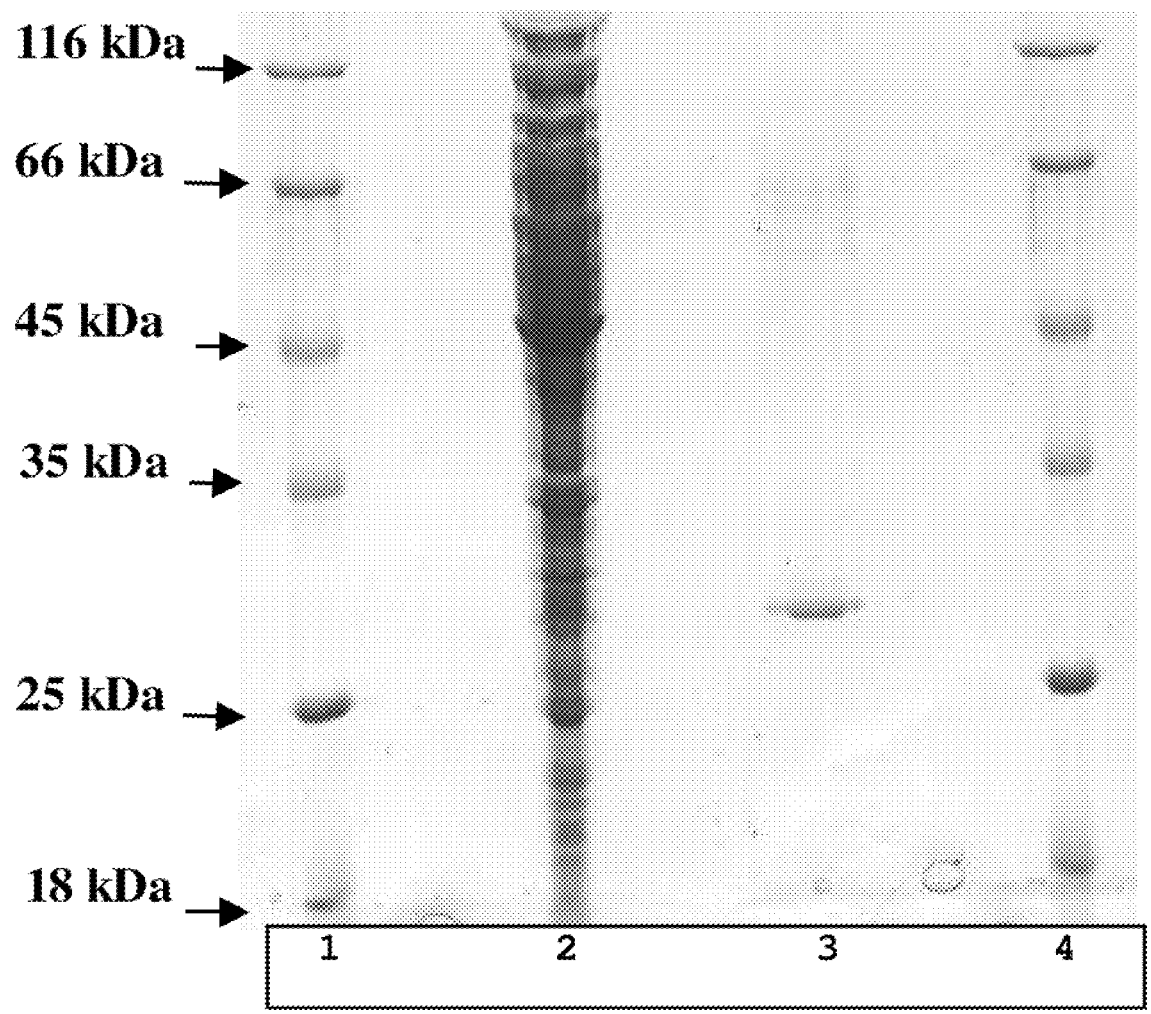
FIG. 2 (photograph) shows purification of HMKP-aldolase from *Arthrobacter simplex* AKU626 (NBRC 12069) (hereinafter abbreviated as asiHPAL). Lanes: 1, 4—protein molecular weight marker (Fermentas, Lithuania). 2—Crude cell lysate (45 μg applied), 3—asiHPAL preparation (0.5 μg applied).

The molecular weight of the asiHPAL monomer was determined using SDS-PAGE (FIG. 2, A). Its average value was estimated to be 27 kDa. The molecular weight of the native asiHPAL was determined using analytical SEC on the Superdex™ 200 HR 10/30A (Pharmacia) columns calibrated by Molecular Weight Protein Markers (Sigma) (FIG. 2, B). Its average value was estimated to be 186 kDa. So, asiHPAL is assumed to be the hexamer.

The dependence of HMKP-aldolase on metal ions was investigated. It was established that asiHPAL activity strictly depends on the $Zn^{2+}$, $Mg^{2+}$ and $Mn^{2+}$ ions and is completely blocked in the presence of EDTA. So, it was assumed that asiHPAL is a Type II aldolases (Table 3).

TABLE 3 asiHPAL activity depending on the $metal^{2+}$ ions.

| | Cofactor (2 mM concentration) | | | |
|---|---|---|---|---|
| Protein | EDTA | $Zn^{2+}$ | $Mg^{2+}$ | $Mn^{2+}$ |
| asiHPAL | ND. [a] | 1 [b] | 0.5 | 0.5 |

[a] non detected
[b] Activities were measured as well as described in the Table 7 footnote. The value of the asiHPAL activity measured in the presence of the $Zn^{2+}$ ion is taken as 1.

Example 2

Determination of asiHPAL N-Terminal Sequence 2.1 Western Blotting of the asiHPAL.

asiHPAL was immobilized on the Sequi-Blot PVDF membrane (Bio-Rad) using trans-Blot SD sell (Bio-Rad). Optimized blotting conditions are as follows: Dun carbonate transfer buffer: 10 mM $NaCHO_3$, 3 mM $Na_2CO_3$ without methanol, six pieces extra thick filter paper/membrane sandwich, starting current 5.5 $mA/cm^2$, transfer time—1 hour).

2.2 Sequencing of N-Terminal End of asiHPAL.

Determination of asiHPAL N-terminal sequence was done using the 491cLC Protein Sequencer (Applied Biosystems, USA). 26 cycles were performed. As the result, the following amino acid sequence was determined:

$NH_2$-Pro-Phe-Pro-Val-Glu-Leu-Pro-Asp-Asn-Phe-Ala-Lys-Arg-Val-Thr-Asp-Ser-Asp-Ser-Ala-  (SEQ ID NO: 3)

Gln-Val-Gly-Leu-Phe-Ile . . . —COOH.

Figure 3:
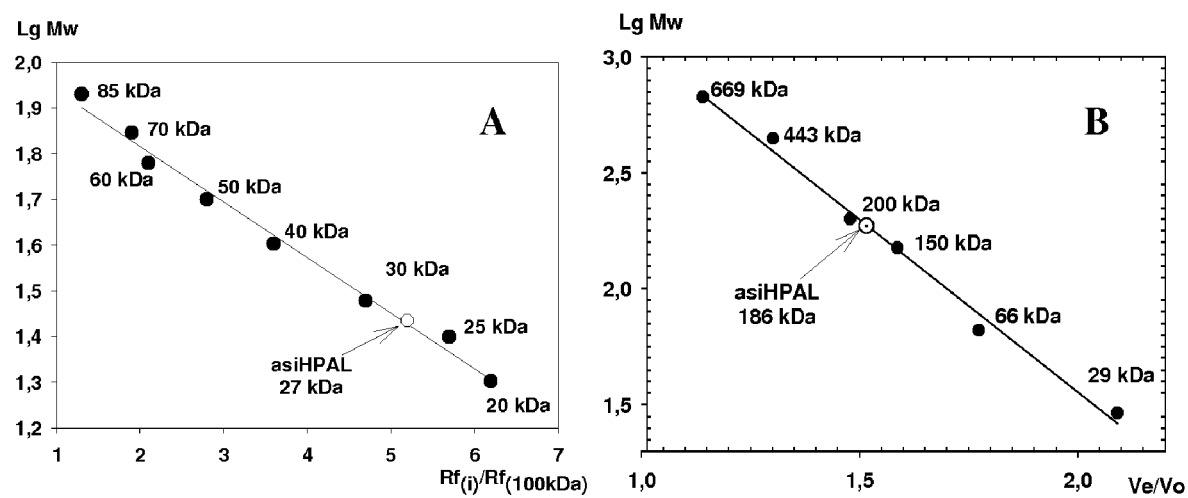
FIG. 3 shows determination of the asiHPAL oligomeric structure. A—Determination of the Mw of the asiHPAL monomer using a calibrated SDS-PAGE gel. PageRuler™ Protein Ladder (Fermentas, Lithuania) was used as protein markers. Experimental data (black circle) were fitted (black line) by linear regression analysis using Sigma Plot 8 software. B—Determination of native Mw of the asiHPAL using SEC on the Superdex™ 200 HR 10/30A (Pharmacia) columns calibrated by Molecular Weight Protein Markers (Sigma). Experimental data (black circle) were fitted (black line) by linear regression analysis using Sigma Plot 8 software.

An alignment of this N-terminal sequence with all known proteins (BLAST search) revealed a single protein with a similar N-terminal sequence. It is the HHDE-aldolase (2,4- dihydroxyhept-2-ene-1,7-dioic acid aldolase) from *Brevibacterium linens* BL2 (HHDE_BLI) (FIG. 3). So, this is a Type II aldolase and its native substrate, 2,4-dihydroxyhept-2-ene-1,7-dioic acid, is structurally similar to HMKP (indeed, both have an hydroxyl group at $C_4$ position, carbonyl group at $C_2$ position, and carboxyl group at $C_1$ position). Moreover, the Mw of the HHDE_BLI subunit is 27 kDa which is consistent with the experimentally obtained subunit Mw of asiHPAL. Also *Brevibacterium linens* is closely related to *Arthrobacter simplex*.

Thus, it could be assumed that asiHPAL purified from *Arthrobacter simplex* is a homologue of HHDE aldolase from *Brevibacterium linens* BL2.

Example 3

Cloning of asiHPAL Gene Encoding HMKP-Aldolase from *Arthrobacter simplex* (NBRC 12069)

To amplify the DNA fragment from the chromosome of *Arthrobacter* simplex which contains the asiHPAL gene, PCR was performed using the degenerative primer asiN10 (SEQ ID NO: 4), which was designed based on the N-terminal amino acid sequence of asiHPAL determined previously (FIG. 4). Primer asiN10 contains a degenerative part on the 3'-end thereof and has a sequence of 21 nucleotides, which are not complementary to the asiHPAL gene. This is necessary for further amplification of the PCR product. PCR was performed in a volume of 40 µl with 0.1 µg of *Arthrobacter simplex* chromosomal DNA and primer asiN10 (20 pmoles). PCR conditions were as follows: 95° C.—10 sec; 53° C.—20 sec; 72° C.—40 sec; 50 cycles.

Figure 5:
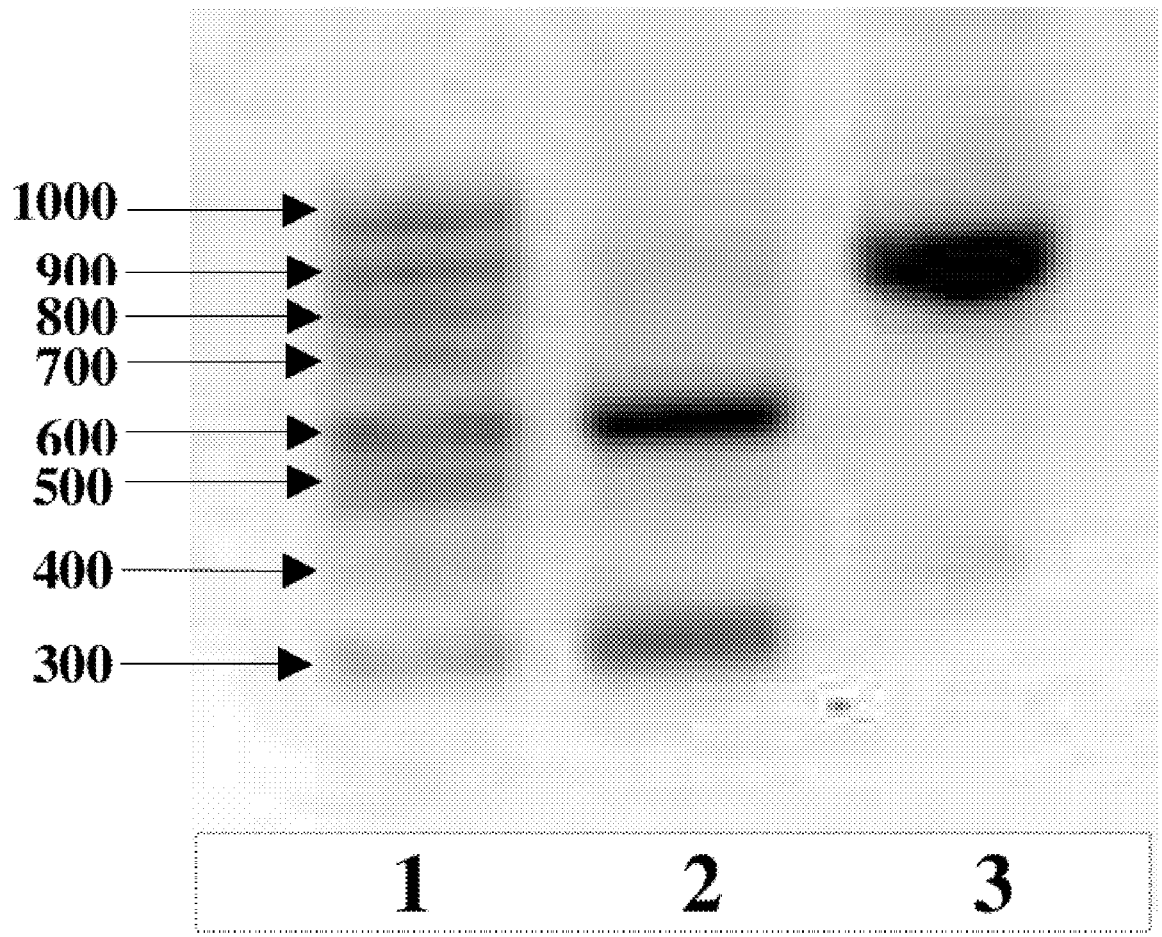
FIG. 5 (photograph) shows amplification of a 0.9 kb DNA fragment of *Arthrobacter simplex* chromosome containing the gene encoding HMKP-aldolase. Electrophoresis of amplified DNA fragment. Tracks: 1—DNA size marker; 3—aliquot of reaction mixture B; 2—resulting 0.9 kb DNA fragment digested by NcoI restrictase.

Surprisingly, as a result of the PCR, a single PCR product was obtained (FIG. 5, track 3). Primer asiN10 appeared to be suitable for use as a forward and reverse primer simultaneously. Furthermore, this was proved by a second round of PCR using the primer SVS88 (SEQ ID NO: 5) (10 pmoles), part of the primer asiN10, which contains the non-complementary 21 nucleotides and 2 µl of reaction mixtures from the first PCR as a template. PCR conditions were as follows: 95° C.—10 sec; 65° C.—20 sec; 72° C.—40 sec; 25 cycles. A strong single PCR product was observed.

Restriction analysis of the PCR product revealed a unique NcoI site which divides the DNA fragment into two fragments: large—0.6 kb and small—0.3 kb (FIG. 5, track 2). Both fragments were sequenced separately using the SVS88 primer. 471 nucleotides of the 0.6 kb fragment and 262 nucleotides of the 0.3 kb fragment were determined.

Figure 6:
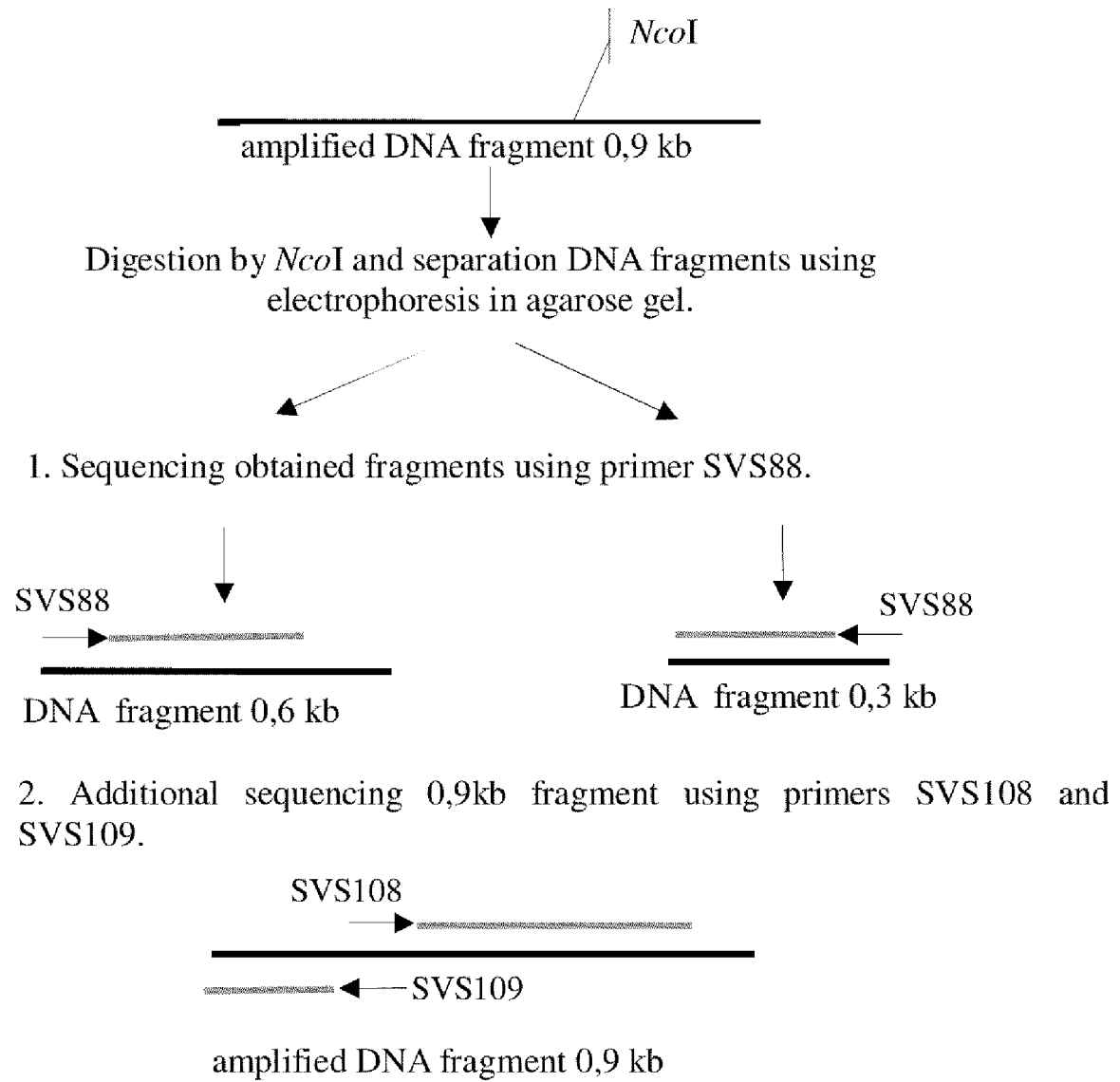
FIG. 6 shows the strategy for sequencing the amplified DNA fragment.

Then, primers SVS_108 (SEQ ID NO: 6) and SVS_109 (SEQ ID NO: 7) were used to complete the sequencing of the entire DNA fragment. The strategy for sequencing the amplified DNA fragment is depicted in FIG. 6. Analysis of the nucleotide sequence revealed that the N-terminal 26 amino acid residues coded by asiHPAL ORF are identical to the N-terminal sequence of asiHPAL determined in Example 2.

An alignment of the ORF with the amino acid sequence of HHDE aldolase from *Brevibacterium linens* BL2 revealed high homology between the enzymes (FIG. 7).

Example 4

Production of 4-hydroxy-L-isoleucine

To test the specific activity of recombinant asiHPAL aldolase coded by the asiHPAL gene from *Arthrobacter* simplex during 4-hydroxy-L-isoleucine production, the asiHPAL gene can be amplified using primers 1 (SEQ ID NO: 8) and 2 (SEQ ID NO: 9), and chromosomal DNA of *Arthrobacter simplex* as a template. Primer 1 contains an HindIII restriction site at the 5'-end thereof, primer 2 contains a BamHI restriction site at the 5'-end thereof. The resulting PCR fragment can be digested with HindIII and BamHI restrictases and ligated into plasmid pMW119, which had been previously treated with the same restrictases. Thus, plasmid pMW119-asiHPAL was obtained. Then, *E. coli* strain BW25113 can be transformed with plasmid pMW119-asiHPAL and the resulting strain BW25113/pMW-asiHPAL can be cultivated in the LB medium containing IPTG (1 mmol).

Formation of 4-hydroxy-L-isoleucine can be tested in the bsuYwaA/asiHPAL bi-enzymatic reaction with the following composition [100 mM L-glutamate (pH 8 adjusted by pH 8.0), 100 mM α-ketobutyrate, 100 mM acetaldehyde], 1 mM $ZnCl_2$, 0.5 µg purified His-tag-bsuBCAT protein (branched-chain amino acid aminotransferase from *Bacillus subtilis*) and an aliquot of BW25113/pMW-asiHPAL cell lysate. All reactions can be carried out at 37° C. Cloning the branched-chain amino acid aminotransferase from *Bacillus subtilis* (bsuBCAT) and HPLC measuring the 4HIL formation are described in the Examples 5 and 6, respectively.

Example 5

Cloning and Efficient Expression of the BCAT from *Bacillus subtilis*

BCAT from *Bacillus subtilis* was cloned and expressed using the pET expression system (Novagen, Madison, Wis., USA) as $his_6$-tag derivatives.

To construct the pET-HT-IlvE-BSU plasmid, the ywaA gene from *Bacillus subtilis* encoding BCAT aminotransferase (Berger, B. J et al, J. Bacteriol., 185(8), 2418-31 (2003)) was amplified by PCR using the chromosomal DNA of *B. subtilis* strain 168 as a template and primers P3 (SEQ ID NO: 10) and P4 (SEQ ID NO: 11) as "upstream" and "downstream" primers, respectively. Primer P5 contains the NcoI restriction site and six codons coding for histidine at the 5'-end thereof, primer P6 contains the NotI restriction site at the 5'-end thereof. The resulting PCR fragment was digested with NcoI restrictase and ligated with plasmid pET-15(b+) which had been previously digested with the same restrictase. Then, the linear ligated DNA fragment was used as a template for PCR-amplification, and oligonucleotides T7 (Novagen, SEQ ID NO: 12) and P4 (SEQ ID NO: 11) were used as a primers. The resulting PCR fragment containing the ywaA gene under the control of T7 promoter of the plasmid pET-15(b+) was digested by XbaI and NotI restrictases and ligated into the pET-22(b+) vector which had been previously treated with the same restrictases. Thus, plasmid pET-HT-IlvE-BSU was obtained. This plasmid was used to transform *E. coli* and His-tag-bsuBCAT protein was purified from the transformant.

Example 6

HPLC Measurement of 4-hydroxy-L-isoleucine

HPLC analysis: High pressure chromatograph (Waters, USA) with spectrofluorometer 1100 series (Agilent, USA) was used. The chosen detection wave range: excitation wavelength at 250 nm, range of emission wavelengths were 320-560 nm. The separation by accq-tag method was performed in a column Nova-Pak™ C18 150×3.9 mm, 4 µm (Waters, USA) at +400° C. Injection volume of the sample was 5 µl. The formation of amino acid derivatives and their separation was performed according to Waters manufacturer's recommendation (Liu, H. et al, J. Chromatogr. A, 828, 383-395 (1998); Waters accq-tag chemistry package. Instruction manual. Millipore Corporation, pp. 1-9 (1993)). To obtain amino acid derivatives with 6-aminoquinolil-N-hydroxysuccinimidyl carbamate, the kit Accq-Fluor™ (Waters, USA) was used. The analysis by accq-tag method was performed using concentrated Accq-tag Eluent A (Waters, USA). All solutions were prepared using Milli-Q water, standard solutions were stored at +4° C.

INDUSTRIAL APPLICABILITY

A novel aldolase is described that catalyzes an aldol condensation reaction of acetaldehyde and α-ketobutyric acid, and may be preferably used to synthesize 4-hydroxy-3-methyl-2-keto-pentanoic acid (HMKP). The aldolase is also useful as an intermediate in 4-hydroxy-L-isoleucine synthesis.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. An isolated DNA selected from the group consisting of:
   (a) A DNA comprising the nucleotide sequence of SEQ ID No: 1;
   (b) A DNA that hybridizes under stringent conditions with a DNA having the nucleotide sequence complementary to the nucleotide sequence of SEQ ID No: 1, and encodes a protein having aldolase activity, wherein said stringent conditions are 0.1×SSC and 0.1% SDS at 65° C.;
   (c) A DNA that encodes a protein comprising the amino acid sequence of SEQ ID No: 2; and
   (d) A DNA that encodes a protein having an amino acid sequence that is at least 95% homologous to the amino acid sequence of SEQ ID NO: 2 and wherein the protein has aldolase activity.

2. A recombinant DNA comprising the DNA according to claim 1 and a vector DNA.

3. An isolated cell transformed with the recombinant DNA according to claim 2.

4. A process for producing a protein having aldolase activity comprising cultivating the cell according to claim 3 in a medium, and accumulating a protein having aldolase activity in the medium, cells, or both.

* * * * *